(12) United States Patent
Bradica et al.

(10) Patent No.: US 10,016,278 B2
(45) Date of Patent: Jul. 10, 2018

(54) BIPHASIC IMPLANT DEVICE PROVIDING JOINT FLUID THERAPY

(75) Inventors: Gino Bradica, Mullica Hill, NJ (US); William Christian Wattengel, West Chester, PA (US); Timothy A. Ringeisen, Exton, PA (US)

(73) Assignee: DSM IP ASSETS B.V., Heerlen (NL)

( * ) Notice: Subject to any disclaimer, the term of this patent is extended or adjusted under 35 U.S.C. 154(b) by 638 days.

(21) Appl. No.: 12/495,611

(22) Filed: Jun. 30, 2009

(65) Prior Publication Data

US 2010/0331865 A1 Dec. 30, 2010

(51) Int. Cl.
*A61F 2/02* (2006.01)
*A61F 2/28* (2006.01)
(Continued)

(52) U.S. Cl.
CPC .......... *A61F 2/28* (2013.01); *A61F 2/30756* (2013.01); *A61L 27/24* (2013.01); *A61L 27/48* (2013.01);
(Continued)

(58) Field of Classification Search
CPC .......... A61B 17/0057; A61B 17/12022; A61B 17/56; A61B 17/562; A61B 17/68; A61B 17/686; A61F 2/0063; A61F 2/28; A61F 2/30756; A61F 2002/30028; A61F 2002/30052; A61F 2002/30332; A61F 2002/30971; A61F 2210/008; A61F 2250/0018; A61F 2250/0051; A61F 2310/00365; A61F 2002/30014; A61F 2002/30031; A61F 2002/30088; A61F 2002/3092; A61F 2002/4495;
(Continued)

(56) References Cited

U.S. PATENT DOCUMENTS 4,186,448 A 2/1980 Brekke
4,187,390 A 2/1980 Gore
(Continued)

FOREIGN PATENT DOCUMENTS

EP 0369034 A1 5/1990
EP 0505634 A1 9/1992
(Continued)

OTHER PUBLICATIONS

Albro, Michael B. et al., Osmotic loading of spherical gels: a biomimetic study of hindered transport in the cell protoplasm, J. Biomechanical Engrg., 2007, 129, 503-510.
(Continued)

*Primary Examiner* — Jing Ou

(74) *Attorney, Agent, or Firm* — Kevin Bull

(57) ABSTRACT

Tissue implants prepared for the repair of tissues, especially avascular tissues such as cartilage. One embodiment presents an electric potential capable of receiving and accumulating desirable factors or molecules from surrounding fluid when exposed to dynamic loading. In another embodiment the implant promotes tissue conduction by retarding, restricting and controlling cellular invasion through use of gradients until competent tissue forms. Further embodiments of the tissue implants may be formed into a multiphasic device that provides deep tissue mechanical stimulus by conduction of mechanical and fluid forces experienced at the surface of the implant.

14 Claims, 7 Drawing Sheets

(51) Int. Cl.
*A61F 2/30* (2006.01)
*A61L 27/24* (2006.01)
*A61L 27/48* (2006.01)
*A61L 27/50* (2006.01)
*A61L 27/52* (2006.01)
*A61L 27/56* (2006.01)
*A61F 2/44* (2006.01)

(52) U.S. Cl.
CPC ............. *A61L 27/50* (2013.01); *A61L 27/52* (2013.01); *A61L 27/56* (2013.01); *A61F 2002/30014* (2013.01); *A61F 2002/30028* (2013.01); *A61F 2002/30031* (2013.01); *A61F 2002/30052* (2013.01); *A61F 2002/30088* (2013.01); *A61F 2002/3092* (2013.01); *A61F 2002/30332* (2013.01); *A61F 2002/30971* (2013.01); *A61F 2002/4495* (2013.01); *A61F 2210/008* (2013.01); *A61F 2220/0033* (2013.01); *A61F 2250/0018* (2013.01); *A61F 2250/0043* (2013.01); *A61F 2250/0051* (2013.01); *A61F 2250/0056* (2013.01); *A61F 2310/00365* (2013.01); *A61L 2430/06* (2013.01)

(58) Field of Classification Search
CPC ..... A61F 2250/0043; A61F 2250/0056; A61L 27/48; A61L 27/52; A61L 2430/06; A61L 27/24; A61L 27/50; A61L 27/56
USPC ................. 623/23.72–23.74; 606/151, 213; 424/422–426; 524/96
See application file for complete search history.

(56) References Cited

U.S. PATENT DOCUMENTS

| | | | |
|---|---|---|---|
| 4,328,000 A | 5/1982 | Horn et al. | |
| 4,642,120 A | 2/1987 | Nevo et al. | |
| 4,708,951 A | 11/1987 | Hiroshi et al. | |
| 4,948,540 A | 8/1990 | Nigam | |
| 5,041,138 A | 8/1991 | Vacanti et al. | |
| 5,116,374 A | 5/1992 | Stone | |
| 5,133,755 A | 7/1992 | Brekke | |
| 5,152,791 A | 10/1992 | Hakamatsuka et al. | |
| 5,166,187 A | 11/1992 | Collombel et al. | |
| 5,306,311 A | 4/1994 | Stone et al. | |
| 5,490,962 A | 2/1996 | Cima et al. | |
| 5,512,600 A | 4/1996 | Mikos et al. | |
| 5,607,474 A | 3/1997 | Athanasiou et al. | |
| 5,686,091 A | 11/1997 | Leong et al. | |
| 5,711,960 A | 1/1998 | Shikinami | |
| 5,716,413 A | 2/1998 | Walter et al. | |
| 5,723,331 A | 3/1998 | Tubo et al. | |
| 5,741,329 A | 4/1998 | Agrawal et al. | |
| 5,759,830 A | 6/1998 | Vacanti et al. | |
| 5,830,493 A | 11/1998 | Yokota et al. | |
| 5,863,297 A | 1/1999 | Walter et al. | |
| 5,876,452 A | 3/1999 | Athanasiou et al. | |
| 5,939,323 A | 8/1999 | Valentini et al. | |
| 5,972,007 A * | 10/1999 | Sheffield ............... A61F 2/0063 606/151 |
| 5,977,204 A | 11/1999 | Boyan et al. | |
| 5,981,825 A | 11/1999 | Brekke | |
| 6,001,352 A | 12/1999 | Boyan et al. | |
| 6,013,853 A | 1/2000 | Athanasiou et al. | |
| 6,027,744 A * | 2/2000 | Vacanti et al. ................ 424/426 |
| 6,065,476 A | 5/2000 | Agrawal et al. | |
| 6,156,068 A | 12/2000 | Walter et al. | |
| 6,203,573 B1 | 3/2001 | Walter et al. | |
| 6,306,169 B1 | 10/2001 | Lee et al. | |
| 6,306,424 B1 | 10/2001 | Vyakarnam et al. | |
| 6,319,712 B1 | 11/2001 | Meenen et al. | |
| 6,344,496 B1 | 2/2002 | Niederauer et al. | |
| 6,365,149 B2 | 4/2002 | Vyakarnam et al. | |
| 6,371,958 B1 | 4/2002 | Overaker | |
| 6,468,314 B2 | 10/2002 | Schwartz et al. | |
| 6,471,993 B1 | 10/2002 | Shastri et al. | |
| 6,511,511 B1 | 1/2003 | Slivka et al. | |
| 6,514,286 B1 | 2/2003 | Leatherbury et al. | |
| 6,530,956 B1 | 3/2003 | Mansmann | |
| 6,534,084 B1 | 3/2003 | Vyakarnam et al. | |
| 6,632,246 B1 | 10/2003 | Simon et al. | |
| 6,669,735 B1 * | 12/2003 | Pelissier ............... A61F 2/0063 606/151 |
| 6,783,712 B2 | 8/2004 | Slivka et al. | |
| 6,858,042 B2 | 2/2005 | Nadler et al. | |
| 7,273,523 B2 | 9/2007 | Wenz | |
| 7,427,293 B2 | 9/2008 | Nycz et al. | |
| 2003/0045943 A1 | 3/2003 | Brekke et al. | |
| 2003/0114936 A1 | 6/2003 | Sherwood et al. | |
| 2003/0129214 A1 * | 7/2003 | Bornstein ............... A61L 27/34 424/423 |
| 2004/0006146 A1 | 1/2004 | Evans et al. | |
| 2004/0133275 A1 * | 7/2004 | Mansmann ................ 623/14.12 |
| 2004/0172048 A1 * | 9/2004 | Browning ............. A61F 2/0063 606/151 |
| 2004/0197311 A1 | 10/2004 | Brekke et al. | |
| 2005/0074481 A1 | 4/2005 | Brekke et al. | |
| 2005/0177118 A1 | 8/2005 | Hoganson et al. | |
| 2005/0261782 A1 | 11/2005 | Hoganson | |
| 2007/0142698 A1 * | 6/2007 | Bourne .................. A61F 2/0045 600/30 |
| 2007/0282455 A1 | 12/2007 | Luginbuehl et al. | |
| 2007/0299542 A1 * | 12/2007 | Mathisen ............... A61F 2/0063 623/23.75 |
| 2008/0249632 A1 * | 10/2008 | Stone et al. .................. 623/23.5 |
| 2009/0043398 A1 | 2/2009 | Yakimicki et al. | |
| 2009/0088846 A1 | 4/2009 | Myung et al. | |
| 2009/0326577 A1 * | 12/2009 | Johnson ............ A61B 17/0057 606/213 |

FOREIGN PATENT DOCUMENTS

| | | |
|---|---|---|
| EP | 0544259 A1 | 6/1993 |
| EP | 0784985 A1 | 7/1997 |
| GB | 2175506 A | 12/1986 |
| JP | 01-232967 | 9/1989 |
| RU | 2146136 C1 | 3/2000 |
| WO | WO 93/15694 | 8/1993 |
| WO | WO 94/09722 | 5/1994 |
| WO | WO 95/11707 | 5/1995 |
| WO | WO 95/31157 | 11/1995 |
| WO | WO-00/09179 A1 | 2/2000 |
| WO | WO 00/55300 | 9/2000 |
| WO | WO 03/008007 A2 | 1/2003 |
| WO | WO-08/088869 A2 | 7/2008 |

OTHER PUBLICATIONS

Ateshian, Gerard et al., A mixture theory analysis for passive transport in osmotic loading of cells, J. Biomechanics, 2006, 39, 464-475.

Ateshian, Gerard et al., A theoretical analysis of water transport through chondrocytes, Biomechanics and Modeling in Mechanobiology, 2007, 6, 91-101.

Ateshian, Gerard et al., A theoretical solution for the frictionless rolling contact of cylindrical biphase articular cartilage layers, J. Biomechanics, 1995, 28, 1341-1355.

Ateshian, Gerard et al., Anisotropy of fibrous tissues in relation to the distribution of tensed and buckled fibers, J. Biomechanical Engrg., 2007, 129(2), 240-249.

Ateshian, Gerard et al., Artificial cartilage: weaving in three dimensions, Nature Materials, 2007, 6, 89-90.

Ateshian, Gerard et al., Finite deformation biphasic material properties of bovine articular cartilage from confined compression . . . , J. Biomechanics, 1997, 30, 1157-1164.

Ateshian, Gerard et al., The role of osmotic pressure and tension-compression nonlinearity in the frictional response . . . , Tranport in Porous Media, 2003, 50, 5-33.

(56) References Cited

OTHER PUBLICATIONS

Chahine, Nadeen et al., Anisotropic strain-dependent material properties of bovine articular cartilage in the transitional range . . . , J. Biomechanics, 2004, 37, 1251-1261.

Chahine, Nadeen et al., Direct measurement of osmotic pressure of glycosaminoglycan solutions by membrane osmometry at room temperature, Biophysical J., 2005, 89, 1543-1550.

Gao, J. et al., Tissue engineered osteochondral graft using rat marrow-derived mesenchymal stem cells, 47 Ann. Mtg., Orthopaedic Research Soc., Ses. 33, 2001, San Francisco CA.

Grande, D. et al., A dual gene therapy approach to osteochondral defect repair using a bilayer . . . , 47 Ann. Mtg., Orthopaedic Research Soc., Ses. 46, 2001, San Francisco CA.

Huang, Chun-Yuh et al., Effects of mechanical compression on metabolism and distribution of oxygen and lactate . . . , J. Biomech., 2008, 41(6), 1184-1196.

Huang, Chun-Yuh et al., The role of flow-independent viscoelasticity in the biphasic tensile and compressive responses . . . , J. Biomech. Engrg., 2001, 123, 410-417.

Hung, Clark et al., A paradigm for functional tissue engineering of articular cartilage via applied physiologic deformational . . . , Ann. Biomedical Engrg., 2004, 32(1), 35-49.

Hung, Clark et al., Anatomically shaped osteochondral constructs for articular cartilage repair, J. Biomechanics, 2003, 36, 1853-1864.

Kisiday, John et al., Effects of dynamic compressive loading on chondrocyte biosynthesis in self-assembling peptide scaffolds, J. Biomechanics, 2004, 37, 595-604.

Kock, Niels et al., Press-fit stability of an osteochondral autograft: influence of different plug length and perfect depth alignment, Acta Orthopaedica, 2006, 77(3), 422-428.

Kou, Ikuyo et al., SOX9-dependent and -independent transcriptional regulation of human cartilage link protein, J. Biological Chem., Dec. 3, 2004, 279(49), 50942-50948.

Lai, W. et al., Electrical signals for chondrocytes in cartilage, Biorheology, 2002, 39, 39-45, IOS Press.

Lai, W. Michael et al., On the electric potentials inside a charged soft hydrated biological tissue . . . , J. Biomech. Engrg., 2000, 122, 336-346, ASME.

Mauck, Robert et al., Functional tissue engineering of articular cartilage through dynamic loading . . . , J. Biomech. Engrg., 2000, 122, 252-260, ASME.

Mauck, Robert et al., Modeling of neutral solute transport in a dynamically loaded porous permeable gel . . . , J. Biomech Engrg., 2003, 125, 602-614, ASME.

Mauck, R. et al., The role of cell seeding density and nutrient supply for articular cartilage tissue engineering . . . , OsteoArthritis and Cartilage, 2003, 11, 879-890.

Park, Seonghun et al., Cartilage interstitial fluid load support in unconfined compression, J. Biomechanics, 2003, 36, 1785-1796.

Park, S. et al., Mechanical response of bovine articular cartilage under dynamic unconfined compression . . . , OsteoArthritis and Cartilage, 2004, 12, 65-73.

Silver, Frederick et al., Mechanobiology of cartilage: how do internal and external stresses affect . . . , Biomechan. Model Mechanobiol., 2002, 1, 219-238.

Wang, Christopher et al., An automated approach for direct measurement of two-dimensional strain distributions . . . , J. Biomechan. Engrg., 2002, 124, 557-567.

Wang, Christopher et al., Optical determination of anisotropic material properties of bovine articular cartilage in compression, J. Biomechanics, 2003, 36, 339-353.

Wang, Christopher et al., The functional environment of chondrocytes within cartilage subjected to compressive loading . . . , Biorheology, 2002, 39, 11-25.

\* cited by examiner

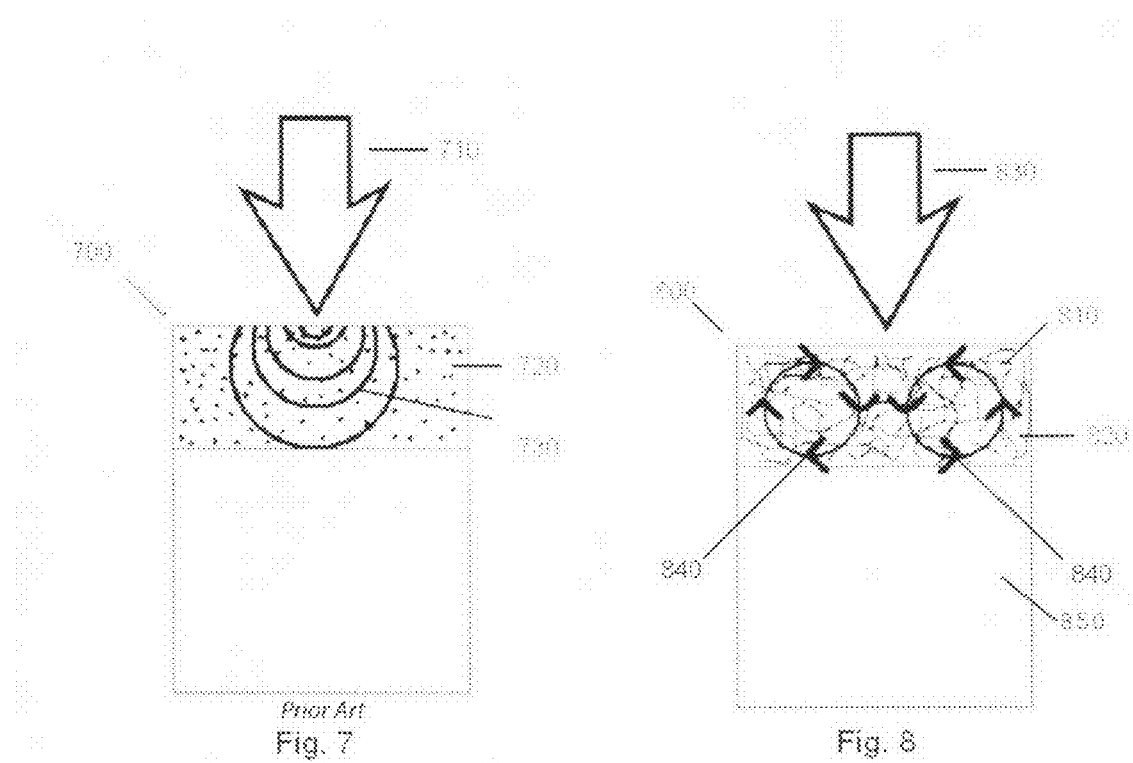
*Prior Art*
Fig. 7
Fig. 8
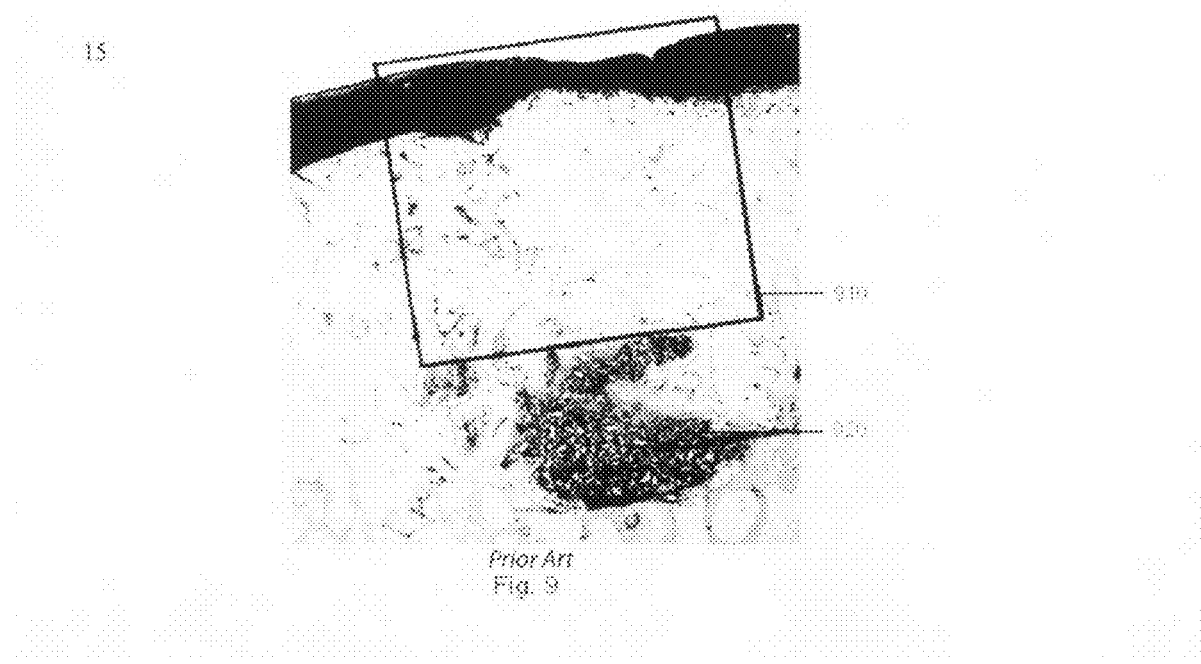
*Prior Art*
Fig. 9

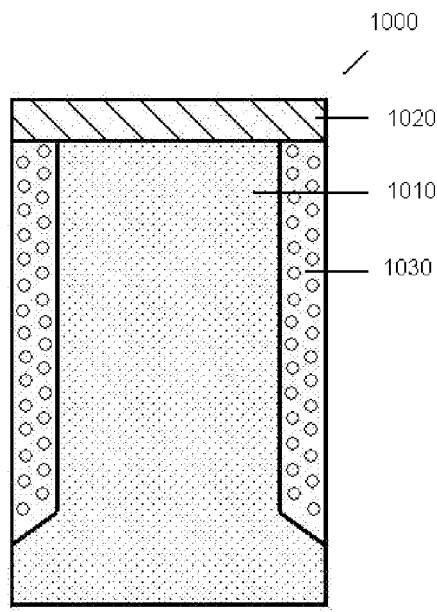
Fig. 10
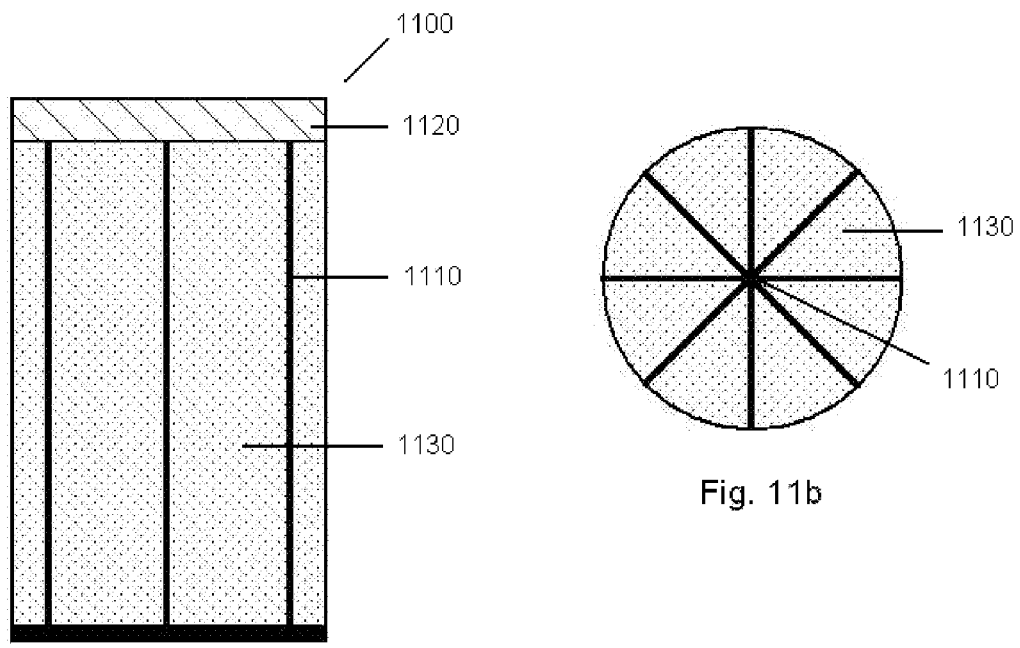
Fig. 11a
Fig. 11b

BIPHASIC IMPLANT DEVICE PROVIDING JOINT FLUID THERAPY

BACKGROUND OF THE INVENTION

What is disclosed is a device for repairing and replacing lost or damaged tissue. Particularly, one embodiment is directed to a multi-phasic prosthetic device for repairing or replacing cartilage or cartilage-like tissues. Said prosthetic devices are useful as articular cartilage substitution material and as a scaffold for regeneration of articular cartilaginous tissues.

Cartilage is found throughout the body, such as in the supporting structure of the nose, ears, ribs (elastic cartilage), within the meniscus (fibrous cartilage), and on the surfaces of joints (hyaline cartilage or articular cartilage). A joint is a bending point where two bones meet. The knee, hip, and shoulder are the three largest joints.

The specialized covering on the ends of bones that meet to form an articulating joint is called hyaline or articular cartilage. It is the cartilage that is damaged and wears as one ages, or sustains an injury. Articular cartilage is unique amongst the body tissues in that it has no nerves or blood supply. This means that damage will not be felt until the covering wears down to bare underlying bone. Bone is very sensitive and the sharp pain of arthritis often comes from irritation of bone nerve endings and since human tissue has a very limited capacity to heal without a blood supply, articular cartilage cannot repair itself effectively.

Articular cartilage tissue covers the ends of all bones that form diarthrodial joints. The resilient tissues provide the important characteristic of friction, lubrication, and wear in a joint. Furthermore, it acts as a shock absorber, distributing the load to the bones below. Without articular cartilage, stress and friction would occur to the extent that the joint would not permit motion. As stated above, articular cartilage has only a very limited capacity to regenerate. If this tissue is damaged or lost by traumatic events, or by chronic and progressive degeneration, it usually leads to painful arthrosis and decreased range of joint motion.

Articular cartilage repair following injury or degeneration represents a major clinical problem, with treatment modalities being limited and joint replacement being regarded as appropriate only for the older patient.

Current treatments for articular cartilage damage are varied and include anti-inflammatory medication, visco-supplementation, arthroscopic chondroplasty, autogenous articular cell implantation, microfracture and osteochondral articular transplantation.

Anti-Inflammatory Medication:

Aspirin was the first anti-inflammatory medication in the world. This was followed in 1950 by cortisone (steroidal medication) used orally or by injection. (Extensive use of cortisone not only has a wide variety of harmful effects, but is also believed to harm cartilage.) Later the non-steroidal drugs such as Motrin came along. These were safer than Aspirin and cortisone but had potent side effects, especially causing bleeding within the stomach and intestinal ulcers. These complications led to the development of the COX-2 inhibitor drugs, Celebrex and Vioxx. While much safer and seemingly more effective, Vioxx was found to have significant cardiac side effects and is no longer available. With certain precautions, Celebrex is still widely used. However, these anti-inflammatory medications only treat the symptoms of cartilage damage and arthritis and do not promote repair.

Viscosupplementation:

Viscosupplementation is a procedure that involves the injection of gel-like substances (hyaluronates) into a joint to supplement the viscous properties of synoval fluid. Currently, hyaluronate injections are approved for the treatments of osteoarthritis of the knee in those who have failed to respond to more conservative therapy. Once again, this procedure only treats the symptoms of cartilage damage and arthritis and does not promote repair.

Arthroscopic Chondroplasty:

Chondroplasty is a term referring to the arthroscopic smoothing of unstable articular surfaces either with mechanical shaving or thermal devices. While not a restorative measure, so called debridement can be useful in reducing irritating cartilage debris that breaks off in the joint or causes catching or grinding sensations. The resulting improvement in the control of inflammation can last for several years. But this is not a final solution as the degenerative process continues to wear away at the articular cartilage.

Autogenous Articular Cell Implantation (ACI):

Autogenous cell implantation can be used for large, shallow defects, which do not involve the subchondral bone. In this procedure, cartilage cells collected from the patient and grown to many millions through cell culture techniques are injected into the joint, under a membrane that has been attached to the cartilage surface. Although successful, the window of opportunity for this procedure is often missed, as the few clinical symptoms showing the need for this treatment are not evident until the defect deepens to involve the underlying bone, thus the damage encountered upon detection is frequently too extensive for repair through ACI.

Microfracture:

The goal of this arthroscopic technique is to improve the blood supply to the bare areas of the joint by creating tiny perforations in the underlying bone. The resulting bone marrow bleeding carries powerful growth stimulating factors found in platelets as well as stem cells to the damaged area creating what is referred to as a super-clot. Healing and repair follow over several weeks. Studies have shown that microfracture techniques do not fill in the chondral defect fully and the repair material formed is fibrocartilage. The fibrocartilage tissue can temporarily return function for activities such as running and a sport play, but ultimately fails, as fibrocartilage is unable to mechanically share and disipate loading forces as effectively as the original hyaline cartilage. Fibrocartilage is much denser and isn't able to withstand the demands of everyday activities as well as hyaline cartilage and is therefore at higher risk of breaking down.

Osteochondral Articular Transplantation:

Osteochondral transplantation (i.e. mosaioplasty) involves transportation of tissue plugs from one location of the knee to another. Special instrumentation has been devised to harvest plugs of articular cartilage and its supporting bone from the patient's own joint. The harvested tissue is then transported to the damaged site where it is inserted into prepared holes. Several plugs can fill up rather larger defects and will grow to re-supply a new joint surface. Unfortunately, this procedure leaves defects of equal or worse proportions elsewhere and often the harvested tissue is not viable due to the traumatic harvesting procedure.

Due to the problems associated with current state of the art treatments, much work has been done to produce a synthetic off-the-shelf scaffold to be used in place of the harvested osteochondral plug.

Originally, single-phase scaffolds of uniform construction were contemplated for use as implants. However, these single-phase scaffold implants proved unsuccessful in healing of the complex multiphasic articular cartilage along with the underlying bone. Soon biphasic and then gradient devices were developed that were either mechanically or anatomically specific for the tissues involved. While these showed an improvement over single phase devices, it is evident that these devices do not take into consideration how cells will be migrating into the scaffolds as well as how their presence influences the surrounding, uninvolved tissue. Additionally, prior art scaffolds did not take into consideration the joint fluid and how it impacts maturation and maintenance of healthy hyaline cartilage. Although prior art synthetic scaffolds, whether single phase, multi-phase, or of gradient construction have proven suitable for growth and maturation of cells within a bioreactor, these prior art devices are unsuitable for direct implantation, for at least the reasons that follow.

Applicants have made the surprising discovery that in effecting the repair of cartilage defects, prior art synthetic implants and synthetic bi-phasic implant devices failed to recognized the need to ignore the normal histological and mechanical gradient of the articular cartilage, and instead focused on the limited cell population surrounding the defect and its slow rate of tissue formation within the devices resulting from this sparse population of cells. The prior art synthetic implants mistakenly focused on speeding up the rate of cell migration within the scaffold in hopes of getting tissue to form rapidly throughout the device prior to collapse of the scaffold. This increased rate of cell migration was done using chemotactic ground substances such as hyaluronic acid, cell seeding or biologics. All this served to do was to spread out the cell population and reduce the rate of hyaline cartilage tissue formation, and as a result, biased any new tissue growth of cartilage towards the fibrocartilage lineage. Although some success in establishing hyaline cartilage can be seen in small defects of 5 millimeters or less, larger defects show tell tale signs of collapse or dimpling in the center of a repair plug, as the less desirable fibrocartilage, which has grown within the prior art devices, succumbs to the forces within the joint. Additionally, prior art devices show a halo or ring of collapsed tissue around the periphery of the device do to lack of intimate contact with the uninvolved tissue that has retracted away from the defect site.

Another discovery of applicants is that prior art devices do not address the instantaneous articular cartilage tissue contraction that occurs when the surface of hyaline cartilage is cut or torn. Upon damage, the cartilage retracts way from the defect site forming a funnel. Thus prior art devices, upon implantation, do not make contact with the surrounding uninvolved cartilage.

The uninvolved host tissue, that is, the normal tissue adjacent to and surrounding the defect site that is not involved with the defect, is able to influence the activities of cells that migrate into and establish themselves at the periphery of a scaffold placed into the defect. The cells of the uninvolved tissue, along with the extracellular matrix of the uninvolved host tissue adjacent to the periphery of the implanted scaffold are already established as hyaline cartilage and thus mechanically and chemically react to stresses appropriately. Through a process, sometimes referred to as mechanical signal transduction, the established host tissue is able to influence the phenotype and extracellular matrix produced by the adjacent cells in the scaffold thus producing the desired hyaline cartilage. Specifically, cartilaginous tissues perform specialized functions under normal physiological conditions. Anomalous mechanical loading of these tissues often leads to pathology. For example, the lack of mechanical stimulation of a joint leads to suppression of proteoglycan synthesis and release of mediators responsible for degradation of cartilage matrix components. This is believed to be the cause of collapse or dimpling of the newly formed cartilage seen with prior art devices.

The molecular mechanisms controlling the response of cartilaginous tissues to their mechanical environment are not completely understood. Furthermore, there is a dearth of knowledge about the modes of mechanical signal transduction in chondrocytes. Several theories concerning the molecular mechanisms through which mechanical stimuli modulate the expression of cartilage extracellular matrix (ECM) components have been proposed, some of which are: 1) receptor mediated cell-ECM adhesion contributes to the transduction of mechanical signals in chondrocytes, 2) mechanical signal transduction in chondrocytes requires activation of the phosphoinositol and/or cyclic AMP (also known as Cyclic adenosine monophosphate or cAMP) signaling pathways, and 3) mechanical stimulation of the expression of aggrecan is mediated through activation of specific cis-acting elements of the promoter and/or UTRs (untranslated regions) of the aggrecan gene. No matter the specific mechanism through which it happens, applicants believe that the influence uninvolved host tissue has over the cells in the scaffold matrix extends approximately 2.5 millimeters. Thus, this places a limit of success for prior art devices having a matrix equal to, or less stiff than the surrounding host tissue to 5 millimeters in diameter. However, any device having a cartilage scaffold matrix greater in stiffness than the surrounding host tissue will not be properly influenced by mechanical signal transduction and will either form calcified tissues or disorganized fibrocartilage that collapses as the matrix degrades and the tissue experiences stress loading.

In order to prevent the observed central collapse or dimpling within the cartilage layer of prior art implants, applicants have discovered that a new type of scaffold must be made that retards rapid migration of cells across the entire diameter of the device, thereby concentrating cells and cell activity at the edges of the device, promoting rapid and systematic tissue conduction and maturation, moving from the outer edge of the device towards the interior. Additionally, the area within the cartilage region of the scaffold where cell activity is occurring must be less rigid than the surrounding uninvolved tissue, to ensure that it is subject to the mechanical influences of the adjacent uninvolved tissue.

Within the bone layer, known prior art devices failed to recognize the impact a rigid scaffold has on the surrounding uninvolved tissue. Whereas malleable elastic scaffolds (scaffolds that can be deformed and then return to their original shape) are desirable for the cartilage layer, rigid stable scaffolds (scaffolds that resist deformation) are required for proper migration and attachment of bone forming cells. However, nearly the opposite conditions are required for stability of existing bone, as micromotion is beneficial to healthy bone structure. Micro-motion and/or stresses are necessary to keep healthy bone from becoming osteopenic. Osteopenia refers to bone mineral density that is lower than normal. Bone mineral density has been shown to drop in healthy individuals who are bedridden, as well as in astronauts who have reduced stress on their skeletal system due to the effects of reduced gravity while in space. As this occurs, the bones lose minerals, heaviness (mass), and structure, making them weaker and increasing their risk of collapse and or breaking. Localized bone mineral density loss has been witnessed due to stress shielding caused by orthopedic rods and plates. During repair of damaged cartilage with prior art devices, voids and osteopenic zones have been observed to form below implanted tissue scaffolds. The theory behind this pathology formation is that stress shielding, caused by the presence of porous tissue scaffolds, results in bone density loss. The scaffolds dampen vibrations that would normally be transferred through the malleable elastic articular cartilage to the calcified region and then conducted deeper into the bone. These conductive forces are necessary for normal bone biology. The conducted forces in normal bone located below an articulating joint travel not only through the bone trabecula, but also through the viscous gel of bone marrow surrounding the bone trabecula. This is because the bone trabecula located under the cartilage of a joint shows a general histologic pattern of elongated channels radiating out from the calcified region into the subchondral bone. Thus forces are not only transmitted down the rigid walls of the channels formed by the trabecula, but are also transmitted by the gelatinous bone marrow contained within the channels. Two functional problems identified with rigid porous scaffolds of prior art devices are as follows. First these rigid devices do not contain elongated channels and thus they tend to dissipate and dampen the hydrostatic pressure pulses that would normally flow through viscous fluids. Secondly these devices are too rigid through the cartilage region thus not allowing for initial compression to establish a pressure wave through the bone marrow.

In order to prevent undesirable bone voids from forming in uninvolved tissues adjacent to the repair device, what is needed is a scaffold capable of transferring forces through the device, and into the tissue. This deep bone mechanical stimulation is due to compression of the articular cartilage region generating mechanical and fluidic forces during normal movement in the joint.

Concerning the synovial fluid, prior art devices fail to recognize the role this substance plays in maintaining healthy articular cartilage. Synovial fluid is a thick, stringy fluid found in the cavities of synovial joints. Synovial fluid reduces friction between the articular cartilage surfaces as well as providing cushioning during movement. The inner membrane of synovial joints is called the synovial membrane and it secretes synovial fluid into the joint cavity. This fluid forms a thin layer (about 50 microns thick) at the surface of cartilage and seeps into the micro-cavities and irregularities in the articular cartilage surface, filling all empty space thus presenting a uniform, smooth surface. The fluid in the articular cartilage effectively serves as a synovial fluid reserve, during movement; the synovial fluid held in the cartilage is squeezed out mechanically to maintain a layer of fluid on the cartilage surface. This so called weeping lubrication ensures that increased friction does not occur as some of the lubrication fluid is swept away during joint movement.

Synovial tissue is composed of vascularized connective tissue that lacks a basement membrane. Two cell types (type A and type B) are present: Type B cells produce synovial fluid. Synovial fluid is made of hyaluronic acid and lubricin, proteinases, and collagenases. Synovial fluid exhibits non-Newtonian flow characteristics. The viscosity coefficient is not a constant, the fluid is not linearly viscous, and its viscosity increases as the shear rate decreases.

Almost all of the protein constituents of synovial fluid are derived from plasma. The passage of plasma proteins to synovial fluid is related to the size and shape of the protein molecule. Most proteins with molecular weights less than 100,000 daltons are readily transferred from one fluid space to another. Thus synovial fluid is a plasma dialysate modified by constituents secreted by the joint tissues. The major difference between synovial fluid and other body fluids derived from plasma is the high content of hyaluronic acid (mucin) in synovial fluid. Normal synovial fluid contains 3-4 mg/ml hyaluronan (hyaluronic acid), a polymer of nonsulfated polysaccharides composed of D-glucuronic acid and D-N-acetylglucosamine joined by alternating beta-1,4 and beta-1,3 glycosidic bonds. Hyaluronan is synthesized by the synovial membrane and secreted into the joint cavity to increase the viscosity and elasticity of articular cartilage and lubricates the surfaces between synovium and cartilage. Both fibroblasts beneath the synovial membrane intima and synovial membrane-lining cells produce this mucopolysaccharide constituent of synovial fluid.

Synovial fluid is believed to have two main functions: to aid in the nutrition of articular cartilage by acting as a transport medium for nutritional substances, such as glucose, and to aid in the mechanical function of joints by lubricating the articulating surfaces. Articular cartilage has no blood, nerve, or lymphatic supply. Glucose for articular cartilage chondrocyte energy is transported from the periarticular vasculature to the cartilage by the synovial fluid. Synovial fluid contains lubricin secreted by synovial cells. Synovial fluid is chiefly responsible for so-called boundary-layer lubrication, which reduces friction between opposing surfaces of cartilage. There is also some evidence that synovial fluid helps regulate synovial cell growth. Synovial fluid serves many functions including: reducing friction by lubricating the joint; absorbing shocks; and supplying oxygen and nutrients to, as well as removing carbon dioxide and metabolic wastes from, the chondrocytes within articular cartilage.

Normal synovial fluid does not clot but may exhibit thixotropy, the property of certain gels to become fluid when exposed to shear forces such as shaking. On standing at room temperature, normal synovial fluid may assume gelatin-like appearance, characterized by higher viscosities. When shaken it will assume a normal fluid nature. Many enzymes have been found in the normal synovial fluid. Alkaline phosphatase, acid phosphatase, lactic dehydrogenase, and other enzymes are present in detectable quantities. Enzymes enter the synovial fluid directly from the plasma or may be produced locally by the synovial membrane or released by synovial fluid macrophages. Synovial fluid also contains phagocytic cells that remove microbes and the debris that results from normal wear and tear in the joint.

Some prior art devices utilize fluid impermeable layers at the cartilage surface, the bone/cartilage interface, or both locations, or have rigid articular cartilage regions resistant to receiving fluid from the synovial space. These types of structures serve as barriers that prevent the normal transfer of essential elements from the synovial fluid, into and out of the cartilage region. What is needed is a device capable of facilitating joint fluid therapy to the chondrocytes within the defect. Joint fluid therapy encompasses delivering, receiving, accumulating and controlling the location of desirable factors or molecules present in the synovial fluid while also delaying or preventing destructive factors, such as digestive enzymes, from prematurely degrading the matrix. These desirable factors or molecules can be those naturally occurring within the synovial fluid or biologically active agents administered into the synovial fluid.

SUMMARY OF THE INVENTION

This invention includes implantable biphasic devices for the repair of tissues of a living being, especially, cartilaginous tissue defects. In the embodiment of a biphasic device, the device has a first region and a second region, each being specific for the growth of a particular tissue type. In an embodiment useful for repair of cartilage defects, the first region is specific for cartilage tissue growth, and the second region is specific for bone growth.

In one aspect of the invention, the device is an electrokinetic implant, in which at least a portion of the device features two juxtaposed materials that form a malleable matrix, where the first material presents a positively charged surface, and the second material presents a negatively charged surface. As the malleable matrix is deformed under the application of pressures, such as may occur while implanted in a living being, an electrical potential is produced as a result of interactions, and interruptions, between the charged surfaces of the first and second materials. In one embodiment, the malleable material will be malleable while hydrated, though it may be rigid, or at least capable of being handled without deformation, while in a dry state. In another embodiment, the malleable material may exhibit an elastic property, tending to return to its original shape after having been deformed. The first material of the malleable materials may be a particulate, especially a fibrous particulate, and the second material of the malleable material may be a hydrogel, such that the particulate is suspended within the hydrogel, and upon deformation, the hydrogel and particulate move relative to each other. The malleable material may be porous. The materials may be ceramics, natural polymers, synthetic polymers, or combinations thereof.

The charges in the charged surfaces may be the result of exposure of the constituent materials to acidic or basic environments, plasma gas, or a result of the attachment of charged substances to the materials.

In one embodiment, the first and second materials of the malleable material are collagen, with the first collagen material, such as a fibrous collagen, presenting a positively charged surface, and the second collagen material, such as a hydrogel presenting a negatively charged surface. In this embodiment, the charged surfaces of the fibrous collagen and hydrogel collagen may be created by exposing each of the collagens to solutions, where one collagen is exposed to a solution having a pH above the isoelectric point of the collagens, and the other collagen is exposed to a solution having a pH below the isoelectric point of the other collagen.

Another aspect of the invention provides for the transmission of forces and loads throughout a malleable matrix component making up at least a portion of the implantable device. In one embodiment, the malleable matrix component is created having a first and second material, where the first material is a hydrogel and the second material is an interconnected network of fibers. In this embodiment, the hydrogel component may be collagen, or hyaluronic acid, and the fibrous component may be collagen or chitosan. The malleable matrix component is able to provide joint fluid therapy to the cells or tissue within the implant device as it is arranged to transmit forces throughout the entire, or at least substantially the entire volume, of the malleable matrix component, as forces applied will cause a vortex ring or gyre due to the interactions of the interconnected fibers pulling on each other, as they are displaced within the hydrogel material. It is believed that the three-dimensional transmission of forces throughout the malleable material will result in the malleable material, or at least the hydrogel component of the malleable material, receiving and accumulating desirable factors or molecules from surrounding fluids, which may be utilized by cells within the device.

In one embodiment, the malleable material is one phase of a biphasic device, and corresponds to the cartilage region, thus the malleable material may be attached to a rigid base corresponding to the bone region. The rigid base material may be metals, polymers, ceramics or combinations thereof. The rigid base may be porous.

In another aspect of the invention, the implant provides for the systematic tissue conduction and growth from the surrounding cartilage tissue, and retards the formation of tissue in the interior of the implant. In this manner, it is believed that the growth of the incorrect type of tissue can be avoided, and better ensure that only the desirable hyaline cartilage is formed. In an embodiment, the device may comprise a gradient, where the gradient is arranged to retard the tissue formation most at or near the center of the implant (when viewed top down), and transitions to little or no retardation of tissue formation towards the perimeter of the implant, adjacent to normal cartilage tissue. The gradient may be in the form of a circular gradient, and may be uniform throughout the device from upper surface to lower surface, or alternatively may vary from top to bottom. The gradient may be a smooth transition or gradual gradient, or alternatively a stepwise gradient having well defined regions within the gradient. The gradient may be a concentration gradient, such as biologically active agents, additives, or combinations thereof. The gradient may be a physical gradient, such as porosity, density, expansion, swelling, elasticity, hardness, compressibility, and combinations thereof. The gradient may be a material gradient, or chemical gradient, such as molecular weight, cross-linking, hydrophobicity, polarity, crystalinity, and combinations thereof. The gradient may be part of the first phase of a multiphasic device, and corresponds to the cartilage region, and may be attached to a rigid base corresponding to the bone region.

In another aspect of the invention, the multiphasic implant provides for the transmission or conduction of pressure forces through the device, down to the underlying bone tissue below the device; in this manner, bone tissue loss below the device, such as may occur due to stress-shielding, may be minimized or avoided. One embodiment of an implant device capable of transmitting such forces would present a bone region presenting a porous material and a rigid penetrating force conductive material capable of transmitting the forces received from a malleable cartilage region to the underlying tissue. The forces to be transmitted may be hydrostatic and directed through channels running through the bone region material, or alternatively force transmission may be in the form of kinetic pressure pulses through the rigid conductive material arranged in the bone phase. The rigid conductive material may be in the form of columns arranged perpendicular to the top and bottom surfaces of the implant, and may flare out to a wider dimension at the junction with underlying bone. The rigid conductive material may be in the form of a rigid multi-facetted web structure oriented perpendicular to the top and bottom surfaces of the implant. In another embodiment, the rigid conductive material is a wedge or cone that transmits the forces through the implant to the underlying bone, but may also transmit some forces laterally as an outward force to the porous bone region material.

In yet another embodiment the multiphasic device capable of transmitting pressure forces presents at least a first material in the form of at least two porous rigid scaffolds, where the first material is separated by at least a second material in the form of a malleable elastic hydrogel, and where the hydrogel is capable of transferring hydrostatic pressure pulses through the bone region of the device in order to prevent bone voids from forming in external underlying bone tissue.

The various embodiments described herein may be at least partially or completely resorbed by the living being. The various embodiments described herein may also feature drugs, biologically active agents, or other additives in all or at least a portion of the device.

Various medical uses of the above-described invention are described below. Other features or advantages of the present invention will be apparent from the following drawings and detailed description of the invention, as well as from the claims.

DESCRIPTION OF THE DRAWINGS

FIG. 7 is a cross-sectional depiction of a biphasic device as found in the prior art, having a cartilage region comprising a gel or porous material.

FIG. 8 is a cross-sectional depiction of a biphasic device, having a cartilage region arranged as a web or matrix, where the web or matrix is able to telegraph applied forces through substantially all of the cartilage region, by the movement of the web or matrix constituents in a manner analogous to a vortex ring, or gyres.

FIG. 9 is a 1-year histology slide of a repair site having had a prior art biphasic implant device implanted, after the device has been completely absorbed, wherein stress shielding is evident.

FIG. 10 is a cross-sectional depiction of an implant embodiment that is arranged to transmit forces or loads through the device to underlying tissue below, using a rigid central column.

FIGS. 11a and b are cross-sectional depictions of another implant embodiment arranged to transmit forces or loads through the device using a stiff, multifaceted web structure and filler porous material.

DETAILED DESCRIPTION OF THE PREFERRED EMBODIMENTS

Figure 1:
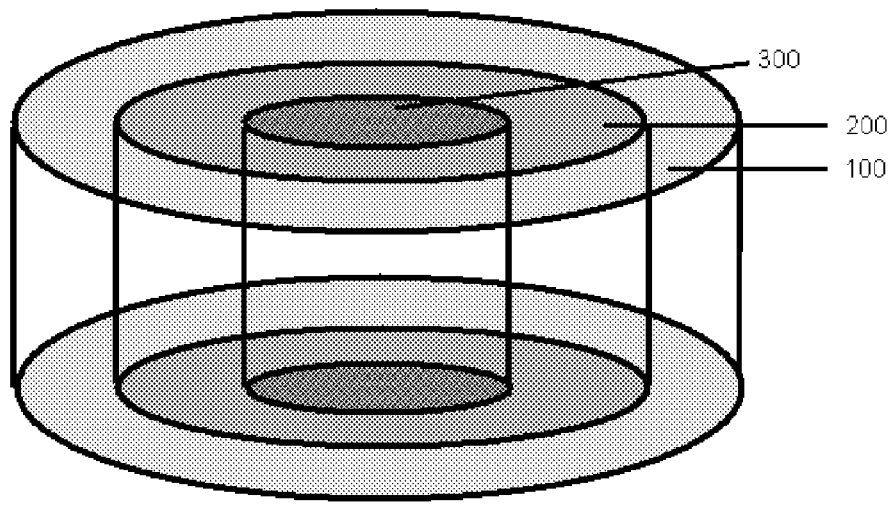
FIG. 1 is a perspective depiction of a circular gradient.

A device and methods are disclosed for treating tissue deficiencies, defects, voids and conformational discontinuities produced by congenital deformities, tissue pathology, traumatic injuries and surgical procedures, particularly those located in mammalian bone and cartilage. In one embodiment, the device is to provide the means by which hyaline cartilage tissue can be conducted across a tissue specific first scaffold region by controlled migration of chondrocytes and/or cartilage precursor cells. Additionally, in an embodiment, the scaffold region can be designed to affect the concentration, location and activity of fluids, factors, molecules or other biologically active agents received from, or delivered to, the extracellular fluids, especially synovial fluid. Thus, the device provides means to regenerate a first specific form of tissue.

A tissue specific second scaffold region may be attached to the first region for controlled migration of osteoblasts and/or bone precursor cells. Thus described, an embodiment of the device is a biphasic device, wherein the device consists of two main parts, the cartilage region, and the subchondral bone region, which are joined at an interface surface. Additionally, an embodiment provides a means for deep bone mechanical stimulus by conduction of mechanical and/or fluid forces originating in, or being applied to the cartilage specific scaffold region. These stimuli will be conducted through the subchondral bone region into the adjacent uninvolved subchondral bone.

In a bi-phasic embodiment, the cartilage region can be joined or bound to the subchondral bone region of the device by a number of processes, including but not limited to, heat fusion, heat welding, adhesives, glues or solvent welding. The resulting union between the two architectural regions is preferably very strong and can withstand any handling required to package the device as well as any forces delivered to it as a result of the implantation technique without permanently distorting the device's internal architecture of void spaces.

The interface surface between the two regions may be a permanent or temporary barrier to the passage of cells, fluids, or biological components (e.g. growth factors, proteins, cells signals, etc.) so long as it does not interfere with the transmission of mechanical stimuli resulting from compression of the first region.

In the biphasic device embodiment, the ingrowth or formation of tissue would be specific to the device region, that is, cartilage tissue would grow into the cartilage region of the device, and bone tissue would grow into the bone region of the device based upon the cells within the immediately adjacent tissues, as well as mechanical and chemical signals provided by the individual layers of the device. Furthermore, each of the cartilage regions and bone regions may provide for a physical structure that is appropriate to the type of tissue for which it is providing a substrate. That is, the bone region will provide a stable substratum for attachment of bone or bone forming cells, while the cartilage region will provide a malleable elastic substratum capable of allowing the surrounding uninvolved tissue to mediate, or affect, the compression and motion of the scaffold adjacent to the host tissue. Additionally, additives capable of enhancing the growth of the target tissue are contemplated within the current invention. Additives in the bone region can include ceramics, glass, glass-ceramics, bioactive glasses, as well as biologically active agents. Additives in the cartilage region can include gelatinous materials, as well as biologically active agents. The additives may be initially loaded into the cartilage region for interaction internally within the device and/or for external device delivery. Additionally, additives can originate within the synovial fluid and be passively or actively transported into the cartilage region of the device. Non-limiting examples of materials and additives useful in construction of the various embodiments of the devices described herein can be found in Table 2.

The architecture of each device region may be formed utilizing established techniques widely practiced by those skilled in the art of medical grade polymers. These methods may include injection molding, extrusion and machining, vacuum foaming, precipitation, sintering, spinning hollow filaments, solvent evaporation, soluble particulate leaching or combinations thereof. For some methods, plasticizers may be required to reduce the glass transition temperature to low enough levels so that polymer flow will occur without decomposition. Additionally additives such as plasticizers or particulates can be added to polymers to make them more or less malleable (malleable materials can be elastic as defined earlier or plastic wherein they do not return to there original shape after deformation) in order to provide the desired mechanical properties for the specific device region they will be located in. For example, a normally rigid polymer may incorporate a plasticizer to make it malleable and thus useful in the cartilage region whereas rigid particles could be added to a malleable polymer to provide a stable substratum suitable for use in the bone region.

In an embodiment, the osteochondral repair device will be formed as a plug, typically circular in cross-section, and shaped to fill a void or defect created through the cartilage layer and into the underlying bone. Additionally, it is recognized that the plug may have a tapered form, such that one end of the device is larger than the other. A defect suitable for accepting the device can be created in a manner known to those skilled in the art, for example, using the device as described in U.S. application Ser. No. 11/049,410, or alternatively using defect creation techniques known as the OATS procedure. It is recognized that alternative shapes other than cylinders, may be utilized, for example joining or overlapping circular elements together into one larger shape will allow for larger defect areas to be repaired with coring tool devices suitable for smaller defects (e.g., approximating an oval, figure eight or a cloverleaf shape). Additionally, non-circular shapes may be utilized as well, such as by providing plug devices with alternative cross-sections, for example, polygonal shapes may be employed or combined (e.g. rectilinear, triangular, hexagonal, etc.), as the polygons may be joined alongside other devices to form a mosaic covering a larger area than could a single device.

Once there is a void created in the bone to accept the implant device (e.g., core created by a coring tool), the implant device is prepared for implantation. The implantable device may be directed into the void through arthroscopic means, or alternatively by hand into the exposed bone void. Preferably, the device is loaded into an insertion tool. Though any known insertion tool or mechanism may be employed, it is envisioned that the delivery can be accomplished with an insertion tool including a device-containing barrel with a delivery end, and also a plunger extending into the barrel for ejecting the device out the delivery end, in a manner similar to a wide mouth syringe. The insertion tool is then placed adjacent to the opening, or directed into the opening, and the device is then ejected from the delivery tool, into the bone void. Preferably, care is taken, both in the creation of the void, and in the delivery of the device, to avoid damaging the healthy nearby tissue, particularly the cartilage tissue and chondrocytes.

Once cellular tissue is fully established within the defect repair site, it is expected that normal loads will be fully supported by the new tissue. For biodegradable devices, the device degrades and is eventually resorbed or removed from the implantation site. This occurs as the device is degraded and provides for the complete transfer of load bearing ability from the device to the ingrown tissue, prior to the device's load bearing ability falling below the levels required to aid in tissue incorporation. Within this document, biodegradable, degradable, bioresorbable, resorbable, bioerodable and erodeble may be used interchangeably.

The various embodiments of a tissue repair device as described herein may be implanted dry, or hydrated with biologically relevant fluids, for example, saline, blood, bone marrow aspirate or Platelet Rich Plasma (PRP). Also, growth factors, hormones, drugs, cells or other useful biologically active agents, can be used to hydrate the device. These materials can provide therapy to the cells migrating into the implant, the surrounding tissue, or the synovial fluid. Optionally, growth factors, hormones, drugs, cells or other useful biologically active agents can be located within the synovial fluid and adsorbed into the implant by passive or active means. For reference, a non-exhaustive list of biologically active agents that may be incorporated into at least a portion or the entirety of the various embodiments contained herein can be found in Table 1.

In healthy osteochondral tissues, for example a knee, having a vertical axis that is in the load bearing direction, and a horizontal axis that is normal to both the tissue surface and the load bearing direction, typically, the encountered loads due to natural movement and gravity are able to be transmitted or conducted through the soft tissues of the joint, and into the hard bony tissues. The load transmission is largely vertical, being in the direction of load application, and creates compression of the soft tissue, however, due to the interconnectivity of the soft tissues, particularly across the transverse layer of the articular cartilage, some portion of the loads are distributed laterally as well, to adjoining soft tissue. One effect of this lateral distribution is that a force of a given magnitude, having been applied at only a small area at the top of the soft tissue, and being transmitted through the soft tissue, would result in the force being distributed over a wider area at the bottom of the soft tissue, and into the bone. Given the wider distribution of the force over a larger area, a compressive force in only a small area of the articulating surface can provide deep bone mechanical stimulus to a large area of subchondral bone, with the peak force felt directly below the originating compressive force and lesser amounts of conductive stimulus radiating outward.

In a similar fashion, where there has been a defect in osteochondral tissue, and a plug device is implanted, the loads that would have normally been transmitted by healthy tissue, would now desirously be transmitted by the plug device as well. Consequently, not only should a device that is inserted into a defect beneficially be able to withstand the expected loads in the defect location, both in the direction of the initial force application, and also laterally as the force is distributed through the soft tissue, but should also be able to adequately transmit or conduct those forces through the device and into healthy adjacent tissues.

Where the device is bioresorbable and also supports the growth of new tissue, it is beneficial to ensure that the degradation characteristics of the device are such that new tissue ingrowth is structurally competent, meaning that it is able to support the expected loads in the defect area, at least coincidentally, or prior, to the degradation of that portion of the device being subsumed by the new tissue ingrowth. In this manner, the device can avoid the dimpling failure mode seen in prior art devices, as a portion of the device becomes structurally incompetent, the newly grown and structurally competent tissues can provide the required weight bearing ability as well as the ability to transmit mechanical stimulus.

One embodiment is intended to address the previously described dimpling failure modes, where, it is believed, a portion of the repaired defect area collapses prior to the growth of structurally competent tissue. It is believed that the collapse manifested as dimpling at the surface of the repair site, is a result of failure in either, or both of, the remaining structures of the implanted device, or in the new tissue ingrowth replacing the device as it degrades. This embodiment alleviates this occurrence by providing for a resorbable implant structure that fosters satisfactory and controlled tissue ingrowth, and provides for the last invaded and absorbed portion of the device to be degraded after the tissue growth in the device is able to withstand and transmit the encountered loads, also termed "structurally competent". This may generally be achieved in one of two broad manners. One may ensure that the device has adequate structural competence for a period of time that is long enough to allow adequate tissue restoration prior to the device becoming structurally incompetent. Alternatively, one may accelerate the radial ingrowth of competent tissue into the device, such that cells are significantly established and forming the morphologically correct tissue, thereby creating structurally competent tissue in a shorter time frame, prior to the device losing its structural competence. There are various techniques that may be employed for achieving each of these goals, such as controlling porosity, density, cross-linking, drug delivery, cell seeding, etc. These techniques will be discussed later. It is recognized that one or more techniques may be combined into a single device, to create an ideal solution.

With reference to the following figures, applicants will describe various embodiments for presenting a tissue repair device. FIGS. 1-6 depict various gradient formations that may be employed within a cartilage region of a biphasic device, that could allow for competent tissue growth to be achieved as the device is degraded and ultimately absorbed, thereby avoiding a mechanical failure of the device caused by collapse or dimpling of the central portion of the newly established tissue within the cartilage region.

In one embodiment, and with reference to FIG. 1, a device is provided having at least one controlled gradient in the device that is arranged concentrically around a vertical axis and normal to the cartilage surface. This circular gradient may provide, for example, for a longer duration of implant structural competence as tissue grows in concentrically (or in the form of accelerated tissue regeneration from the outer zone) and spreads to the inner zone depicted at the center of the device and whereas the zones depicted in the outer portion of the device allows for rapid cell invasion and the inner central zones retard cell invasion, or extracellular matrix deposition, until such a time as the cells in the outer zones have laid down the appropriate extracellular matrix, influenced by the mechanical reaction to loading of the uninvolved adjacent cartilage, in the form of hyaline cartilage. It is important to prevent the occurrence of tissue formation as isolated islands, which are not in contact with the uninvolved normal articular cartilage, as isolated islands will not receive appropriate mechanical stimulus from the surrounding uninvolved tissue.

Figure 2:
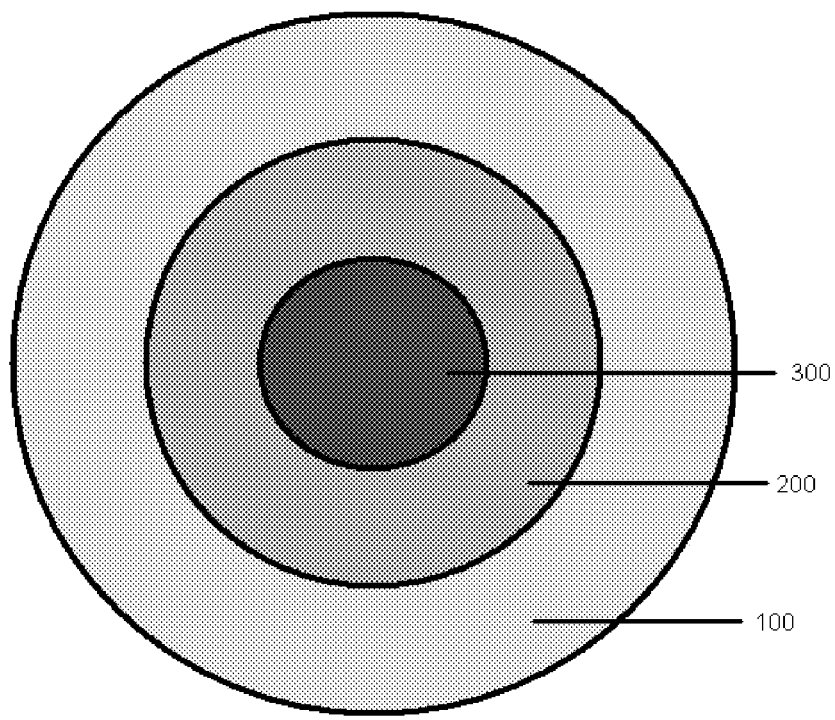
FIG. 2 is a cross-section depiction of the circular gradient of FIG. 1.
Figure 3:
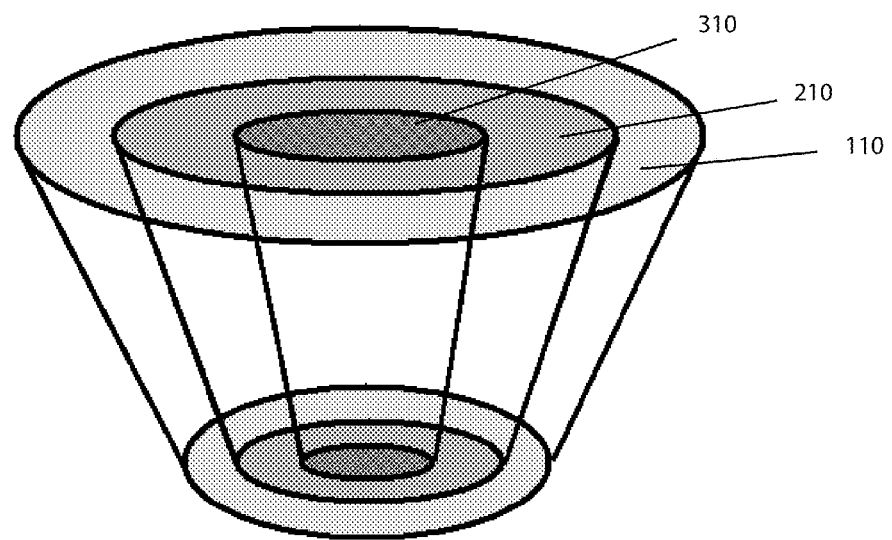
FIG. 3 is a perspective depiction of a circular gradient having a tapered construction from upper surface to lower surface.
Figure 4:
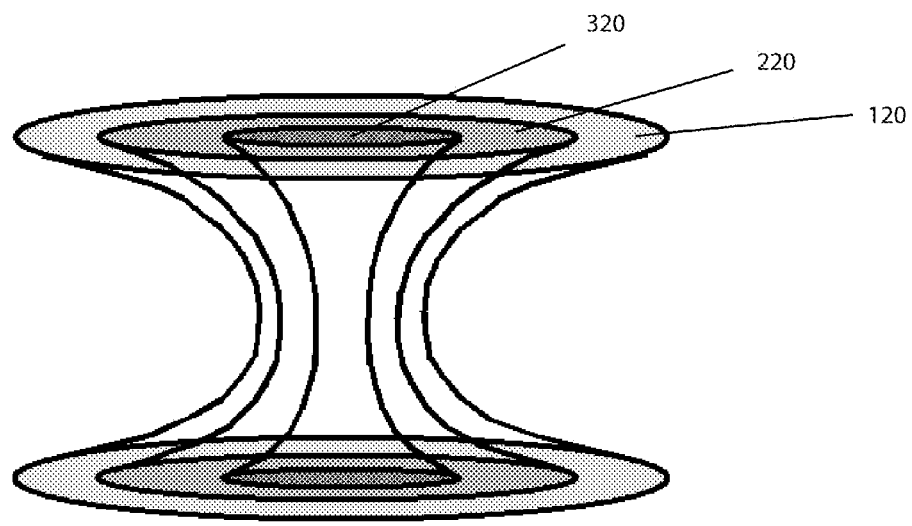
FIG. 4 is a perspective depiction of a circular gradient having an hour-glass shape, wherein the gradient zones are wider in the upper and lower surfaces, and featuring a narrow mid-section.

The controlled circular gradient in the device of FIG. 1 is termed a "bull's-eye" gradient. The "bull's-eye" gradient refers to the way the device appears when viewed from the cross-sectional direction depicted in FIG. 2. As can be seen, the bull's-eye gradient consists of a central core region or zone 300, surrounded by one or more annular rings. In this depiction, there are two annular rings, 100 and 200, concentrically arranged about the central core. Though it is recognized that more or less annular rings could easily be achieved as well. The controlled gradient depicted in FIG. 1 with the cross section as shown in FIG. 2 is uniform throughout the length of the device. It is also contemplated that the gradient could vary along the vertical axis, for example, differing in dimension to provide non-uniform cross-sections throughout the length of the device, as can be seen, for example in FIG. 3 and FIG. 4. In FIG. 3, the gradient has two annular rings 110, and 210, surrounding a core region 310. In FIG. 4, the gradient has two annular rings 120, and 220, surrounding a core region 320. It is recognized that the gradients depicted by the figures may exist within a separate structural element in the form of a cylinder or disk.

Gradients can fall into many different groups including but not limited to concentration, chemical, physical and material. The invention can be provided in a great variety of useful shaped devices, as will be discussed later, where the gradients of the invention may be created by varying one or more of a variety of characteristics, including porosity, density, molecular weight, cross-linking, hydrophobicity, hydrophilicity, polarity, drug concentration, drug delivery, material, expansion, swelling, elasticity, hardness, compressability, crystallinity, cell seeding, etc. To provide further clarity, select characteristics will be explored more fully below, with reference to FIG. 1, as the simplest embodiment, however, it is recognized that other shapes or gradient forms for practicing the invention could employ similar characteristic or compositional gradients.

Controlling the density of specific regions of the device may be useful to provide greater structural resistance to compressive loads. In an embodiment, a gradient can be constructed where the center of the device has a higher density then the outer edge. The density change may be achieved, for example, by varying any of the porosity, pore size or pore number in each region of the device, or by varying the molecular weight of the polymer in various zones. For the example of a bull's-eye gradient, as depicted in FIG. 1, the device may provide higher density polymers or less porous scaffolding at the center zone 300, and then further removed from the center to the perimeter on the cross-sectional plain of the device, the material becomes less dense and more porous. This embodiment with high porosity at the outer zone 100, allows for the cells to migrate quicker initially at the outer zone 100, but retards their ability to reach the central zone 200 and inner zone 300, thus concentrating the cells in the outer zone 100. Central zone 200 will have a porosity or density in between that of the interior and exterior of the device. This will also extend the duration of structural competence at the core, as the mechanical strength of the core is elevated due to the increased density, and can thus be tailored to stay above a minimum threshold value (as determined by the expected physical loading in the defect area) for a longer period of time, as the device goes through biological degradation. The increased duration of structural competence at the center zone 300 allows more time for tissue to infiltrate, grow, and become structurally competent in the core of the device, prior to the total degradation or structural collapse. Those skilled in the art will recognize other types of gradients that can be used to decelerate cellular migration, as will be discussed.

An embodiment of the device may provide for a gradient by using biologically active agents (e.g., drugs, cells, growth factors, etc), ceramics, glass, metals or polymers, all of which are included in the term "additives" incorporated into the device. In this embodiment, the outer zone 100 of the device may provide an elevated additive concentration, relative to the additive concentration provided at the central zone 300 of the device. For the specific case of growth factors, or other agents that will enhance cellular chemotaxis and growth, this high concentration in the outer zone 100 will help recruit cells to the outer edge of the device faster and can increase tissue regeneration at the exterior of the device, resulting in a shorter time period to reach structural competence as the new tissue continues to grow into the middle zone 200, and then into the core zone 300.

Controlling the rate of cross-linking of the polymer in specific regions of the device may be useful to provide greater structural resistance to compressive loads. In an embodiment, a gradient can be constructed where the innermost zone 300 of the device has a higher percentage of cross-linked polymers than the outer zone 100 with middle zone 200 having a percentage of cross-linked polymer somewhere in-between. As a result of the cross-linking, the polymer will be more stable under loads, and less subject to biodegradation and bioresorption, resulting in a longer duration of structural competence in the more extensively cross-linked regions, relative to the lesser cross-linked regions of the device. This increased resistance to compressive loads will protect any cells prematurely gaining access to the core portion of the cartilage region from receiving incorrect mechanical signals prior to being influenced by the encroaching tissue. Cells receiving little to no mechanical stimulus will either attempt to move down the bone lineage line (i.e., differentiate), or if isolated from high oxygen content as naturally occurs in the articular cartilage, will remain relatively dormant while waiting for mechanical or chemical stimulus. In this way the innermost, more cross-linked region will not inadvertently allow cells to commit to the bone or fibrocartilage line, but instead cause the cells to wait to be influenced by the mechanical properties of the tissue being conducted through the matrix from the outer zones as the matrix degrades and becomes softer. With reference to FIG. 1, the core zone 300 may be a highly cross-linked polymer, and transition to outer zone 100 that is not cross-linked at all, or features less cross-linking. As stated previously, mechanical signal transduction is critical to differentiation of the newly forming tissue, any device having a cartilage scaffold matrix greater in stiffness than the surrounding host tissue will not be influenced by mechanical signal transduction and will either form calcified tissues or disorganized fibrocartilage that collapses as the matrix degrades and the tissue is stress loaded. Thus it is important to initially concentrate the tissue forming cells in the outer zones where they can be influenced by the surrounding uninvolved tissue while at the same time preventing premature collapse of the central zone. The device as described herein is intended to set up the best circumstances to allow for the formation of the correct tissue type.

Controlling the compositional makeup of specific regions of the device may be useful to provide regions with longer durations of structural competence. In an embodiment, a gradient can be constructed by controlling the polymer blend ratio in each of the zones to provide varying mechanical strength, or degradation rates. For example, the innermost zone of the device may be manufactured with a polymer or a blend of polymers that provides enhanced resistance to degradation, or increased mechanical strength, when compared to the polymer, or blend of polymers provided in the outer zone of the device. In this embodiment, the center core of the embodiment will feature an enhanced duration of structural competence relative to the outer zone of the device.

As a specific non-limiting example, and with reference again to FIG. 1, natural polymers such as collagen may be used to create regions with varying durations of structural competence. The outer zone 100 of the device can be constructed from soluble collagen that posses no fibers and is gelatinous by nature. This allows for more rapid cellular tissue in-growth to the outer region of the device as the collagen has a low compressive modulus and/or degrades at a rapid rate allowing the newly recruited cells to be stimulated by the mechanical forces necessary to lay down the appropriate tissue matrix. The middle region 200 of the device may be constructed from fibrillar collagen. Being of a higher hierarchical structure the fibrillar collagen provides greater structural integrity and/or greater resistance to degradation. In the core zone 300 the collagen may be fibrous, thereby providing even greater mechanical properties and/or greater resistance to degradation than either of the outer zones. Thus, using the hierarchical structure of collagen, a gradient can run through the spectrum of gelatin, soluble collagen, fibrillar collagen, fibrous collagen and collagen in the form of decellularized tissue, with or without its extracellular matrix components, some or all of which can be cross-linked as a tool for further control. Additionally, the gradient could be based on length and/or thickness and/or density of fibrils or fibers. For instance a homogenous soluble collagen disk may contain an additive such as collagen fibers with the mass or density of said collagen fibers increasing as one proceeds or travels from outer zone 100 towards inner core 300. Collagen gradients, as well as other material gradients, may also be the result of differing animal sources (bovine, porcine, equine, etc), or use of genetically engineered collagen, for instance from plant sources.

Regions with varying durations of structural competence may also be achieved with different types or species of polymers from natural or synthetic sources. As an example, outer zone 100 can be made from hyaluronic acid, which is very easily degradable, while the middle region 200 can be constructed from natural polymer that is more resistant to degradation such as collagen. The inner core 300 may contain an even tougher polymer such as chitosan. Non-limiting examples of materials and additives useful in construction of devices described herein can be found in Table 2.

Figure 5:
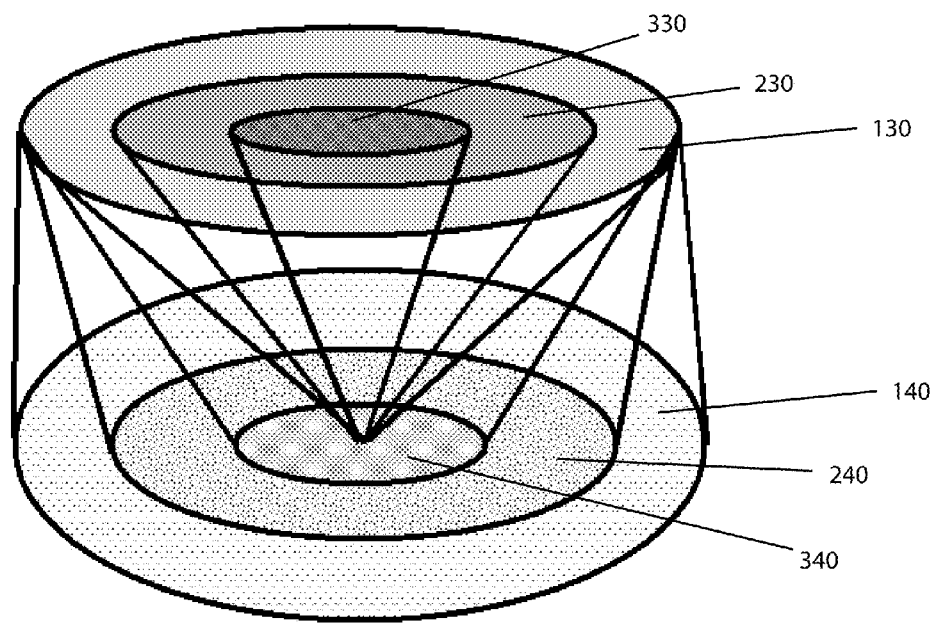
FIGS. 5 and 6 are perspective depictions of multiple circular gradients within the same device.
Figure 6:
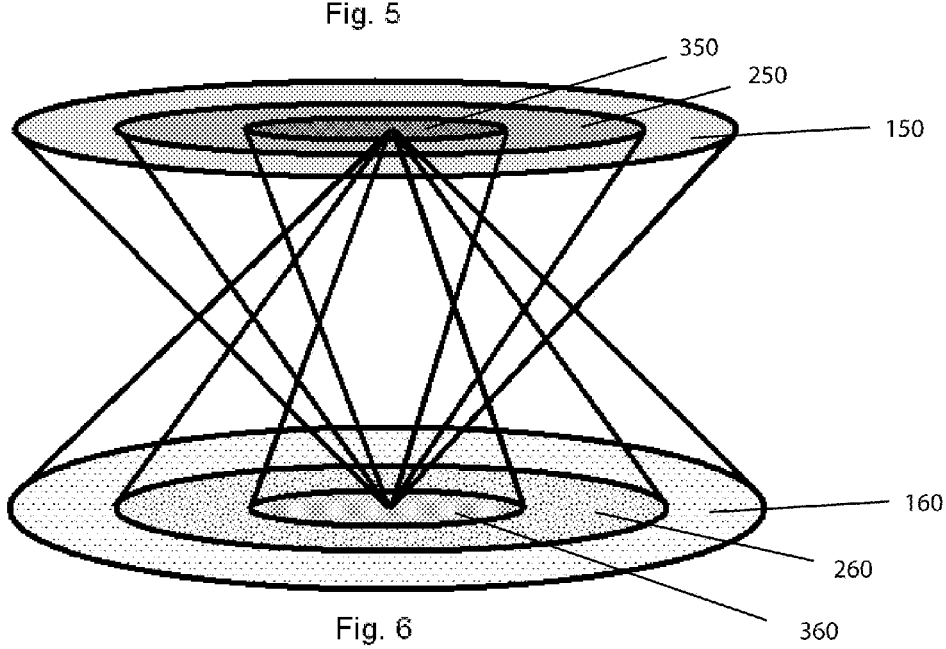

It is recognized that various embodiments of the device may provide more than one gradient, examples of which are depicted in FIGS. 5 and 6. In these multi-gradient embodiments, a pair of gradients are created, a first bull's-eye gradient may extend from its widest dimension at the upper surface, and as one travels down the vertical axis, the bull's-eye of the first gradient is shown to diminish in cross-section, ultimately contracting to a point where the zones merge. The second gradient may extend from the lower surface, and diminish in area as one travels up the vertical axis.

Specifically with regard to the multiple gradient embodiment, as depicted in FIG. 5, the first gradient has two annular rings 130, and 230, surrounding a core region 330, and the second gradient has two annular rings 140 and 240, surrounding a core region 340. As can be seen, the second bull's-eye gradient has its largest dimensional area at the lower surface, and as one travels up the vertical axis, the bull's-eye gradient forms around the cone formed by the first bull's-eye gradient described previously. Thus the outer dimension of the second gradient is shown to remain uniform, while the inner zone of the second gradient forms as an annular ring surrounding the cone of the first gradient. As one nears the upper surface of the device, the second bull's-eye gradient regions merge into a narrow annulus, preferably at or near the upper surface of the device.

Specifically with regard to the multiple gradient embodiment, as depicted in FIG. 6, the first gradient has two annular rings 150, and 250, surrounding a core region 350, and the second gradient has two annular rings 160 and 260, surrounding a core region 360. As can be seen, the second gradient is created as an inverse to the first gradient, and has its largest dimension at the lower surface, and as one travels up the vertical axis, the bull's-eye of the second gradient is shown to reduce in cross-section, ultimately reducing to a point where the zones merge. In this embodiment, the first and second gradients are composed of unrelated characteristics or materials, and the presence of one gradient will not necessarily interfere with the presence of the other, thus they can be seen to overlap or extend into each other as depicted in FIG. 6. It should be recognized that these gradients might exist within a device having the gross shape in the form of a cylinder. For example, a plug device having a uniform porosity with one of the gradientsbeing a first biologically active agent, and the other gradient being a second biologically active agent. In another example, one of the gradients may comprise a structural gradient (e.g., density, cross-linking, etc.)

A potential application of this "reverse-cone" of FIG. 5, or "inverse-cone" of FIG. 6 is that the gradients can be employed to optimize the balance required between promoting rapid cell regeneration and tissue competence, against the required need for adequate mechanical competence of the device as well as regulating the rate of device degradation, which is so important to the success of the device. In this embodiment, it is believed that the first gradient (upper) could preferably be a density gradient, such as can be created by controlling the porosity, pore size, pore density, or polymer molecular weight, and the second gradient (lower) could preferably be an additive gradient (e.g., growth factors, drugs, ceramics, cells, etc.)

Yet another "bull's-eye" design can have a narrow midsection creating an hourglass look, as depicted in FIG. 4. (It should be noted that this depiction only represents the gradient, such as mechanical integrity resulting from fiber incorporation, and that the general matrix in which the gradient resides is not pictured.) The cross-section in this area of the device gradient is much smaller, relative to the upper and the lower regions of the device gradient, but still maintains the "bull's-eye" pattern. In such an embodiment, the mechanical integrity of the device is maintained by the gradient depicted. Thus the gradient may not always occupy the entirety of the device to be implanted. This extra area not pictured can be filled, for example, with highly porous polymers that aren't required to provide any structural competence properties, and whose main objective would be to receive host cells and thus promote more rapid tissue regeneration in the external regions closest to the uninvolved host tissue. That is, for the external regions where little or no structural competence is required to be provided by the device allowing the uninvolved adjacent host tissue to mechanically influence the region, it is preferable to provide a material that maximizes the amount and extent of cellular ingrowth into the exterior of the device, in order to provide a foothold of structurally competent tissue within the device as quickly as possible.

For controlled gradients generally, it is contemplated that the gradient be formed by altering some material or property within the device in a manner corresponding to the patterns depicted in the figures. Starting from the innermost zone at the core and transitioning through the intermediate zones out to the outer region, the gradient would provide some characteristic that varies as one moves further out from the center. For the sake of simplicity and ease of visualization, much of the explanation in this application only discusses the example of FIG. 1, however, it is recognized that the teachings of this application also are applicable to the other examples and figures contained in this application as well.

As depicted in FIG. 1, the gradient may feature zones delineated by the concentric annular rings that provides a recognizable or detectable border or interface between each of the differing zones presented by FIG. 1. Alternatively, it is recognized that a continuous transitional gradient or gradual circular gradient could be provided, where there is a gradual change in the characteristic, from the core region and progressing out to the outside circumference, and the rings depicted in FIG. 1 are merely representative of the direction of the transition.

It is envisioned that a device providing for the various gradient characteristics described herein could be manufactured as an intact device, using carefully controlled lyophilization techniques for creating these gradients. Alternatively, a series of components may be manufactured, each varying in a particular characteristic. Subsequently, the components may be shaped to a form, where each component will form one of the zones, and thereafter be assembled into a final device. For example, and with reference to FIG. 1, a core piece could be manufactured, and later inserted into annular rings sized concentrically, where each of the assembled components will create the gradient desired in the final device. Alternatively, one component may be provided as a scaffold material in the manufacture of the other components, thereby forming a multi-zoned device providing a gradient characteristic. An example of this manufacturing method would include the injection molding of a central skeleton followed by the incorporation of other less dense open-celled matrices whose densities progress from the central structure outward towards the perimeter of the finished device.

It is also envisioned that gradients could be made or created by compressing a starting porous polymer matrix to collapse or sacrifice pores and thus develop a device having the various zones as previously described. In addition, these gradients could be developed by starting with granulated material, and then through the use of heat and compression, could yield a finished device containing varying porosities and physical shapes. For example, fine granular material having an average diameter less than 50 microns can be placed in the center of a cylindrical mold creating a central core. Around this can be pored a medium granular material having an average diameter in the range of 50-100 microns creation a middle zone. A course granular material having an average diameter exceeding 100 microns in turn will surround this. Compression and heat may then be used to fuse this granular material together to create a bull's-eye gradient device.

It is also contemplated that the cartilage region of the current invention could be made to expand after implantation. In this manner, the device would provide intimate contact with the surrounding uninvolved cartilage tissue that has retracted away from the defect hole, as the removal of a circular defect from normal articular cartilage has been observed to result in differential retraction of the edges. Depending on the depth of the defect, the edges retract more in the superficial zone as compared to the deeper zones after a circular defect is removed with a punch. Normal human cartilage, with an intact superficial zone, curls when removed from the underlying bone. The retraction away from the defect site, as well as the curling of the removed cartilage, is the result of the high tension existing within the superficial zone of articular cartilage. This results in a cone or funnel shape forming in the articular cartilage portion of a surgically created defect, narrowing as one moves down towards the subchondral bone portion of a surgically created defect. The current invention anticipates this and thus can be capable of radial expansion in order to ensure a tight fit. For example, a cylindrical device can be place into a newly created defect and expand until is has a shape as shown in FIG. 3.

Applicants have made an additional surprising discovery that in effecting the repair of cartilage defects, prior art synthetic implants and synthetic bi-phasic implant devices failed to recognize the importance of synovial fluid in the maintenance and repair of articular cartilage. As an additional consideration in the development of a device for repair of articular cartilage one needs to understand how friction, cyclic motion, electric potential and synovial fluid all work together to maintain the articular cartilage phenotype. Under normal physiological conditions, articular cartilage provides a nearly frictionless surface between moving joint. To help lubricate these joints, the body uses synovial fluid. This fluid component consists primarily of water with dissolved solutes and mobile ions.

Solute transport in biological tissues is a fundamental process of life, providing nutrients to cells and carrying away waste products. In avascular tissues such as adult articular cartilage, solute transport occurs primarily across the articular surface, with synovial fluid mediating exchanges with the synovium lining the joint capsule. A primary mechanism of solute transport is through diffusion. The mechanism of passive diffusion in healthy cartilage has been shown experimentally to be enhanced by cyclical loading of the cartilage, and by electro-osmotic flow both, of which mechanisms lead to convective flow within the tissue. Other avascular tissue types that respond similarly to articular cartilage include tendon, ligament, meniscus and annulus thus the techniques described herein for use in cartilage repair by manipulating the natural fluid and electric potential in the region may be used on these other tissue types as well. It is also envisioned that these techniques could be beneficial on vascularized tissue that are elastic in nature, including but not limited to blood vessels and skin.

Within cartilage, it is recognized that the synovial fluid acts as a transport medium for substances into and out of the articular cartilage region. This is necessary because the articular cartilage region is a non-vascular tissue. Substances are transported into and out of the articular cartilage region due to repetitive mechanical stimulus followed by a period of rest. During active mechanical stimuli, molecules located within the synovial fluid are actively transported into the articular cartilage layer. This allows the concentration of molecules within the cartilage tissue to exceed that of the synovial fluid. During rest, the concentration will return to equilibrium. In this way, necessary substances located within the synovial fluid are forced into the cartilage tissue, whereupon the cells can absorb them. Waste products are excreted by the cells into the interstitial space of the tissue where they build up. During a period of rest, the system moves towards equilibrium and thus the waste products move out of the cartilage tissue and into the synovial fluid wherein they are ultimately transported into the vasculature and away from the knee.

Thus, vital nutrients are supplied to the non-vascular or avascular tissues from the blood vessels located at the margins of the tissue. The transport of nutrients through the dense complex extracellular matrix to the cells making up these tissues relies mainly on diffusion. Poor nutrient supply has been suggested as a potential mechanism for degenerative processes that affect the avascular tissues (i.e.—osteoporosis, disk degeneration, etc.) and is also suspected in failure of prior art cartilage implants.

The effects of dynamic compression on chondrocyte biosynthesis have been well characterized in cartilage explants and chondrocyte-seeded scaffolds. In explants, continuously applied dynamic compression and dynamic tissue shear have been found to increase synthesis of proteins and proteoglycans.

Studies of articular cartilage metabolism have demonstrated that static loading, as well as loading below a characteristic frequency of 0.001 Hz, leads to biosynthetic inhibition, whereas dynamic loading stimulates tissue synthesis. This enhanced biosynthetic response is believed to result from an enhanced nutritional supply, as well as a tissue biosynthetic response under dynamic loading, and thus resulting in enhanced fluid flow and changes in cell shape or mechanotransduction. Static compression of articular cartilage has been shown to reduce the diffusivity of various solutes within the tissue, and has been implicated in the altered biosynthetic response of the tissue to static loading. Growth factors, which have been shown to regulate the biosynthetic response of articular cartilage, are generally large solutes with molecular weights on the order of tens of kilodaltons. A further benefit of dynamic loading is growth-factor uptake. It has been shown that dynamic compression accelerates the biosynthetic response of cartilage to free IGF-I and increases the rate of transport of free IGF-I into the cartilage matrix, suggesting that cyclic compression may improve the access of soluble growth factors.

Dynamic compression, thus, augments the transport of solutes in avascular tissues such as cartilage. However, the effect of mechanical compression on the distribution and metabolism of nutrients is difficult to directly evaluate. To this end, research has been conducted on synthetic gels in order to answer these questions.

Exposing an agarose gel, submerged in a fluid medium containing target molecules, to repetitive mechanical compression can crudely simulate the dynamic tissue compression system. It has been observed that although the target molecules move against the concentration gradient onto the gel, they are not evenly distributed throughout the gel. The molecules only move into the area under direct mechanical stimulus. If it was the case that cartilage tissue behaved identically, then it would follow that cells around the edges of the cartilage, would be deprived of necessary substances. However, as will be discussed, cartilage does not behave identically to agarose gel, though it does exhibit the similar phenomenon of increasing the concentration of molecules as a result of repeated compression. This unequal distribution of necessary substances is a shortcoming of prior art devices having a gel-like property within the cartilage region. Normal articular cartilage overcomes this unequal distribution by having a dense fibrous layer, known as the transverse layer that absorbs and distributes mechanical stimulus across the entirety of the tissue layer by providing a mechanical coupling of the cartilage molecules to each other. In this way, necessary substances are actively moved into the entirety of the cartilage tissue layer.

Similar to the normal cartilage tissue layer, a preferred form of the current invention allows for uniform incorporation of necessary target molecules by providing a biodegradable, insoluble malleable elastic gel or hydrogel like substratum containing a sufficient concentration of fibers so that they form a penetrating interconnected phase. The gel or hydrogel can also present an interconnecting porosity. The fibers, making up a second phase can be entangled, entwined, interwoven, knitted or in some other fashion connected in a three-dimensional web or matrix so that stresses in the form of a push or pull are telegraphed throughout the entire device. In this way the current invention is capable of receiving joint fluid therapy throughout its entire volume.

FIG. 7 represents prior art biphasic device 700 having a cartilage region of simple pores, or in the form of a gel. When force 710 is applied to the surface of cartilage region 720, pressure waves 730 remain focused just below original force 710. Contrasted with the embodiment of FIG. 8, which depicts a cross-section of biphasic device 800 wherein connected fibers 810 are located within layer 820. Layer 820 corresponds to the cartilage region of biphasic device, and is attached to rigid base 850, corresponding to the bone region. When force 830 is applied to the surface of layer 820, downward pressure force 830 causes connected fibers 810 to pull on each other, telegraphing pressure force 830 throughout the entire volume of layer 820, creating a circular force, vortex, vortex ring, toroid, or gyre, as represented by arrows 840. It should be noted that although shown in a single plane, the described circular force occurs three-dimensionally establishing a vortex ring, that is, multiple vortexes or gyres within the device. The potential vorticity of fluid within the device is directly related to the volume of displacement within the device matrix from the downward pressure force. In the simplest sense, vorticity is the tendency for elements of the fluid to "spin." and can be related to the amount of "circulation" or "rotation" in the fluid contained in the matrix caused by the gyres. As new host tissue grows into the edges of this embodiment of the device, forces applied to cartilage tissue distant from the device will be transmitted through the host tissue and into the device.

The cartilage layer of an embodiment of the device will be composed of at least two phases. This first phase is an insoluble gel or hydrogel capable of adsorbing and concentrating target molecules from the synovial fluid when placed under repetitive compressive forces. The second phase will be a fibrous component associated with or contained within the gel phase having sufficient connectivity so that a compressive force applied to one location of the cartilage layer is transmitted throughout substantially the entire volume of the cartilage layer. In order to achieve this the minimum average fiber length for fibers randomly located within the gel should be approximately equal to the thickness of articular cartilage, which is from 2-3 millimeters in length. The maximum average fiber length should not exceed 1.5 times the diameter of the devices so as to prevent curling or coiling of the fibers preventing them from being taut within the matrix and thus dampening the transmission of mechanical stimulus. These same length restrictions apply to interwoven or knitted type devices in as much as connecting nodes or knots holding the structure together should be no closer than 2-3 millimeters apart and no farther apart than 1.5 times the diameter of the devices. For the example of a plug implant device having a diameter of 10 mm, and a cartilage region thickness of 3 mm, the average length of the fibers would be in the range of 2-15 mm, and the average distance between connecting nodes or knots would be in the range of 2-15 mm.

The material phases can be fabricated from natural and/or synthetic polymers including but not limited to collagen, elastin, keratin, chitosan, hyaluronic acid, silk, alginate, polyethylene glycol (PEG) and combinations thereof. (Non-limiting examples of materials and additives useful in construction of devices described herein can be found in Table 2.) One or more of the phases can also contain biologically active agents such as those listed in Table 1.

The biologic activities of the chondrocyte population are regulated by genetic, and other biologic and biochemical factors, as well as environmental factors. It has often been noted that physical environmental factors, such as stress, fluid flow, electric fields, etc. are as strong as biologic factors in regulating cellular activities. There has been much research on the effects of mechanical and/or hydrostatic/osmotic pressure loading on cartilage explant metabolism. Such studies have been specifically aimed at elucidating possible "mechano-signal" transduction (also referred to as "mechanotransduction") mechanism(s) that might govern the chondrocytes' biosynthetic activities in maintaining and organizing the extracellular matrix (ECM) comprising the tissue. Over decades many researchers have observed electrical events in cartilage, but few studies have focused on the details of the electrical potential within the ECM where the chondrocytes reside. This phenomenon of electromechanical or electrokinetic cell signaling has also be ignored by prior art devices. Electromechanical or electrokinetic cell signaling is not to be confused with mechanotransduction, as mechanotransduction does not create electrical potential.

The electromechanical signals that chondrocytes perceive in situ are the result of stresses, strains, pressures and the electric fields generated inside the extracellular matrix when the tissue is deformed. The potential induced by convection in the presence of a pressure gradient in deformed tissue is the "streaming potential". The potential induced by diffusion in the presence of a concentration gradient in static tissue is the "diffusion potential".

Avascular tissues such as cartilage are composed of water, collagen enmeshed in a proteoglycan gel, and various matrix proteins. The osmotic pressure of these tissues is mainly due to the high density of charged carboxyl and sulfate groups on the glycosaminoglycans of the proteoglycans within the tissues. When avascular tissues are deformed under loading, interstitial fluid flow occurs, even though the hydraulic permeability of the tissues is very low. The electrical response of the tissues also changes when it is compressed due to the effects of diffusion potential and streaming potential.

The diffusion potential is the electric potential caused by the separation between the bulk positive and bulk negative charges caused by the gradients of mobile ions within the different fluid regions of the tissue or between the tissue fluid and the synovial fluid.

Streaming potential is defined as the difference in electric potential between a diaphragm, capillary, or porous solid and a liquid that is forced to flow through it. The definition of streaming potential can also include the difference in electric potential caused by the oscillation, separation or flow of a gel in relationship to a diaphragm, capillary or porous solid. Specifically, it is the potential that is produced when a liquid or gel is forced to flow through a capillary or a porous solid. The streaming potential is one of four related electrokinetic phenomena that depend upon the presence of an electrical double layer at a solid-liquid/gel interface. This electrical double layer is made up of ions of one charge type that are fixed to the surface of the solid and an equal number of mobile ions of the opposite charge which are distributed through the neighboring region of the liquid/gel phase. In such a system the movement of liquid/gel in relation to the surface of the solid produces an electric current, because the motion of the liquid/gel causes a displacement of the mobile counterions with respect to the fixed charges on the solid surface. The applied potential necessary to reduce the net flow of electricity to zero is the streaming potential. Streaming potential is related to zeta potential by factors that include the electrical conductivity and fluid/gel viscosity. The value of streaming potential under given conditions of conductivity and pressure can be used to judge how strongly the tissue will interact with anionic or cationic molecules. The zeta potential is a good predictor of the magnitude of electrical repulsive force. A resulting voltage is measured between electrode probes on either side of a boundary. This voltage is then compared with the voltage at zero applied pressure.

The source of electrical events, as measured on the outside surface of normal articular cartilage, derives from the fixed, immobilized or trapped negative charges ~$SO_3$ and $COO_2$, distributed along the chondroitin, keratin sulfates and hyaluronan molecules comprising the aggrecan inside the extracellular matrix of the tissue. These proteoglycans may be assumed to be "immobilized and trapped" inside the extracellular matrix, and therefore considered to be fixed to the extracellular matrix. Together with the surrounding collagen network, these proteoglycan macromolecules form the cohesive, strong, porous-permeable, charged, collagen/proteoglycan solid matrix. By virtue of the electro-neutrality law, there is always a cloud of counterions (e.g., Ca, Na) and co-ions (e.g., Cl) dissolved in the interstitial water surrounding the fixed charges in the extracellular matrix. These ions may move by convection with the interstitial fluid due to a hydraulic pressure or by diffusion through the fluid due to a concentration gradient or by conduction, drifting through the fluid as a current due to an electric field. Forces for the electric current inside the tissues include the mechano-chemical force generated by the gradient from movement of ions resulting from compression and diffusion caused by ion concentration gradients.

Within deformable tissues such as articular cartilage, intervertebal disk, epiphyseal (growth) plate, and cornea, the electric fields resulting from mechano-chemical forces are constantly present. Thus, for such tissues, both streaming potential and diffusion potential must always exist inside the tissue and in fact they always compete against each other. The streaming potential arises from the slight separation of the bulk of the positive charges from that of the negative charges due to the flow convection effects caused by a pressure gradient from deformation of the tissue. The diffusion potential arises from the slight separation of the bulk of positive charges from that of the negative charges due to diffusion caused by the gradients of mobile ions. It is believed that electrical events inside the tissue are important in stimulating chondrocyte biosyntheses. It is also believed that non-uniform electrical effects resulting from deformation occurs when a tissue is softened during a disease process such as osteoarthritis. In osteoarthritic cartilage, with matrix degradation, the intrinsic compressive stiffness always diminishes, thus affecting chondrocyte deformation and metabolic activities as well as the nature of the mechano-electrochemical events within cartilage when it is deformed.

Another preferred embodiment of the current invention presents a cartilage region that takes into consideration both diffusion potential and streaming potential in its constructions. The cartilage layer of this preferred device will be composed of at least two phases. This first phase is an insoluble gel or hydrogel capable of adsorbing and concentrating target charged molecules from the synovial fluid when placed under repetitive compressive forces. The second phase will be a fibrous component contained within the gel phase having sufficient connectivity so that a compressive force applied to one location of the cartilage layer is transmitted throughout the entire volume of the cartilage layer. This allows creation of a disparity between the overall charges of the synovial fluid from that of the cartilage layer establishing the diffusion potential. In addition to this it is desirable for the first phase to predominantly contain either positive or negative charges while the second phase will predominantly contain charges opposite that of the first phase. In this way a pressure gradient from deformation of the cartilage layer of the preferred embodiment creates a slight separation between the charges of the first phase from that of the second phase, as the gel and fibers flex, thus establishing the streaming potential. If desirable, one or both phases can be cross-linked. Thus the electric potentials created by such an embodiment simulate that which occurs in normal articular cartilage, thus improving and/or stimulating chondrocyte biosyntheses and thus articular cartilage tissue formation.

In one possible method for the manufacture of an embodiment that takes into consideration both diffusion potential and streaming potential, insoluble collagen fibers are exposed to a more basic chemical environment (above the pH of the collagen's isoelectric point) in order to bring the surface of the collagen above its isoelectric point and thus providing a predominantly negative charge to the surface of the fibers composing the second phase of the devices. These negatively charged fibers are embedded within a collagen gel or hydrogel that was exposed to a more acidic chemical environment (below the pH of the collagen's isoelectric point) so as to drive this collagen below its isoelectric point to provide a predominantly positive charge to this first phase. This is unlike prior art devices that contain two phases of collagen wherein both collagens are on the same side of the isoelectric point.

In another embodiment, biodegradable polyester fibers (ie—PLA, PGA, PCL, etc), which have been subjected to surface modifications, such as exposure to acids, bases, or plasma gas processes) are used in the second phase of the device.

In another embodiment, hyaluronic acid gel or hydrogel having a predominantly negative charge is used as the first phase that encapsulates and surrounds a second phase of chitosan fibers having an overall positive charge. When making combinations such as hyaluronic acid and chitosan, care must be taken so that a polyelectrolytic complex (PEC) is not formed as this will not allow the charges to separate during compression and thus no electric potential will occur.

In another embodiment, an electrically neutral hydrogel first phase envelops a charged fibrous second phase, wherein the gel allows mobile ions to penetrate and take up residence within the gel thus balancing out the charge of the fiberous second phase. As described previously, deformation of the combined matrix will result in charge separation, creating the electric potential. An example of an electrically neutral hydrogel would be a PEC. Such a PEC could be manufactured by various techniques known in the art, incorporating known components. The neutral hydrogel PEC could be created by the combination of charged components, such as hyaluronic acid-chitosan, collagen-chitosan, and hyaluronic acid-collagen.

It is also recognized that the second phase material can be composed of particulate materials that are not fibrous or polymeric in nature so long as they provide the necessary charged surface. A non-limiting list of materials suitable for this use can be found in table 2.

Those skilled in that art will identify other combinations of positively and negatively charged materials all of which are embraced by this disclosure for use in creation of an electro-kinetic tissue repair device.

As already discussed, in some embodiments, part of the function of the device is to transfer forces or loads, experienced by the cartilage layer, through the devices and into the subchondral bone. This deep bone mechanical stimulus is necessary to prevent stress shielding that currently results in bone voids below the device. FIG. 9 shows 12-month histology from a prior art device that provided stress shielding to the underlying bone. Box 910 shows the approximate location of the implant that has completely resorbed. Soft tissue void 920 within the bone is the result of this stress shielding.

Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. Research into bone healing has shown that some mechanical stimulation can enhance the healing response and it is likely that the optimum regime for a cartilage/bone graft or construct will involve different levels of loading over time in order to properly repair a damaged region. This same observation was concluded by Surgeon Julius Wolff back in the 19$^{th}$ century and is still known today as Wolff's law.

Many prior art implants that are made for use in repairing damaged bone and cartilage are fabricated from soft materials and deform when they are implanted into a cored hole in the bone. These implants do not provide a means for the transfer of loading through the implant for stimulating the growth of new bone at the bottom or side walls of the cored hole, or even controlling or preventing osteopenia or osteoporosis. Other implants that are fabricated as bone void fillers are made from rather stiff materials such as ceramics. These devices can provide a means for mechanical stimulation; however, the implant must be precision fitted to the bone void in order to create the proper length to match up with the hole that has been cored into the patient's bone. Since any protrusion of these devices will result in higher contact pressure, which may further damage the cartilage in joint areas, it is not advisable to use these devices for cartilage repair.

For osteochondral transplantation involving the replacement of damaged cartilage sites with harvested plugs taken from the patients' joint, it is also difficult to match the cored hole depth with the exact implant length. This is a function of the design of the coring tool as well as the technique utilized by the surgeon. For some coring tools, the cored hole will exhibit a very uniform cylindrical shape, however, the bottom surface may be inconsistent and have a rather jagged and irregular surface. This can create gaps or void pockets under the implant or create a void between the top of the implant and the mating rotating bone and prevent any transfer of forces or pressure during the healing process. In addition, the surgeon is concerned about protrusion of the harvested plug creating too much pressure on the transplanted hyaline cartilage thereby damaging this tissue as the joint moves. Therefore, the surgeon often creates a deeper recipient site defect then the length of the harvested plug. This allows the surgeon to control the final position or height of the implanted device; however, this is assuming that the frictional forces alone will provide enough stability for the plug to stay in position. This also creates a void space under the implant, which prevents contact from occurring with the subchondral bone.

Other studies have shown that bottoming out the implant can provide for better support and stability during the time that the cells are growing into the newly implanted plug. However, bottoming out the implant can cause high compressive forces during insertion, which can also damage the transplanted cartilage during the surgery. These same studies have also shown that these implanted plugs are more stable and can be cut to shorter lengths if they are bottomed out.

In order to obtain loading through the cartilage/bone region of any device, contact and pressure are required to exist. As previously discussed, it may not be possible to create a tight enough fit between the implanted device and the cored hole in the patient's bone. Therefore, the implanted device needs to provide the capabilities to expand and contract to fill this space.

Based on these requirements, it is envisioned that a device could be designed so that a portion of it has the ability to expand and contract like an extension spring. Once the device is implanted into a cored hole, the expansion and contraction of the implant would provide the proper functionality. In addition, it is desirable to also create sufficient contact with the walls of the cored hole.

A cartilage/bone repair device is envisioned which takes into consideration the transfer of structural loads or pressures that may be seen by the implant once it is installed into a cored-out hole in the recipient's bone.

In various embodiments, the implant may be made of different materials or different forms of the same material. As an example, a rigid support skeleton can be injection molded from a PLA polymer and this same polymer can be chemically processed to create an open-celled foam structure. Both of these materials would act in completely different ways in regards to their absorption characteristics, their load transfer characteristics, and their biological cell attraction characteristics.

In other embodiments, the implant may include various means of securing itself within the area of bone repair. These securing means can include mechanical methods such as teeth or ridges that are incorporated around the outside surfaces of the device. These teeth or ridges can also assist with the transfer of forces through the device and into the surrounding bone.

In further embodiments, the device could utilize different characteristics formulated into the structural make up of the device in order to promote the take up of fluid thereby causing a hydraulic effect in a portion of the device, which would create a means of expansion and thereby allow for pressure to be transferred through the device.

In another embodiment, the device contains fluid swellable expansion zones that provide for a tight fit within the void and allow for micro-motion while other porous stable zones allow for cell attachment and tissue growth.

Various methods can be utilized for transferring the forces or loads through the device in order to provide mechanical stimulation to the bone interfacing surfaces. As shown in FIG. 10, device 1000 has center column 1010 positioned under cartilage layer 1020 that transcends down the center and then transitions to a larger diameter at the bottom to allow the transfer of force or pressure between the upper surface of the implant and the implant/bone interface layer at the bottom of the device. Porous matrix 1030 surrounds center column 1010 and makes contact with the host tissue. Center column 1010 can be porous, but is rigid and thus conductive of mechanical stimulus that would be dampened by porous matrix 1030. It is preferable that porous matrix 1030 swells shortly after placement into the tissue void so direct contact is made with the tissue void walls. In addition transitioning to a larger diameter at the bottom, center column 1010 can also transition to a larger diameter at the top (not shown), presenting an hourglass type of shape. Additionally, center column 1010 can be formed from a small diameter cylinder with a thin flat plate on the bottom and optionally the top (not shown). The porosity, if present, in center column 1010 can be random, or in the form of elongated channels capable of conducting hydraulic forces.

FIG. 11a shows device 1100 having multi-facetted web structure 1110 that is oriented perpendicular to the top and bottom surfaces of device 1100. In this configuration, the web acts as a stiffener to transfer the load originating in cartilage layer 1120 through the implant. Secondary material 1130 is a less dense, more porous structure formed in between the spokes of web structure 1110. FIG. 11b shows a top down view with the cartilage layer removed so that the relationship of the spokes of web structure 1110 and secondary material 1130 can easily be visualized. In this embodiment, the web would continue to transfer the forces into the subchondral bone region while bone growth was occurring within the porous structure of secondary material 1110 found in between the webs or spokes of web structure 1110. As bone growth completed the encroachment of this area, it would assist with the load or pressure transfer while the materials of web structure 1110 started its degradation and eventual removal. Web structure 1110 can have holes or slots within its structure to allow intercommunication of the secondary material 1130.

Figure 12:
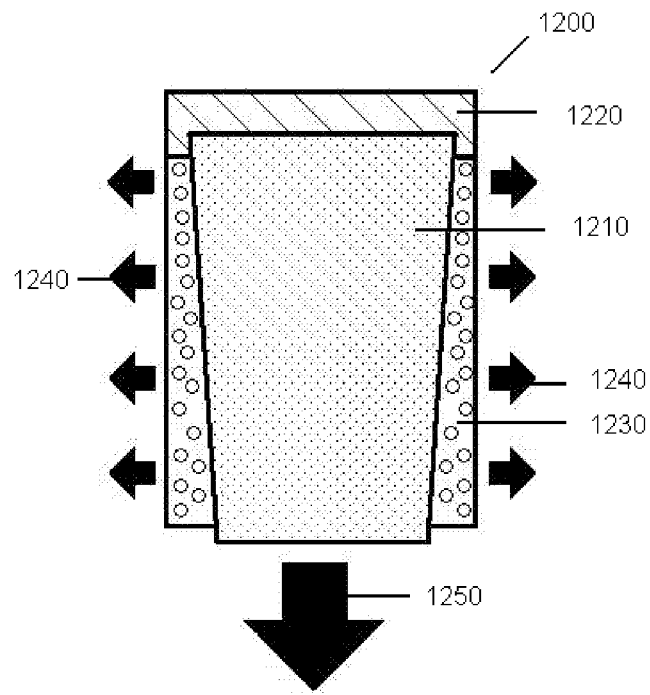
FIG. 12 is a cross-sectional depiction of an implant embodiment that is arranged to transmit forces or loads through the device using a rigid central conically shaped center post.

As shown in FIG. 12, device 1200 has conically shaped center post 1210 sitting below cartilage layer 1220. Center post 1210 wedges into outer cylinder layer 1230 possessing a shaped inner cavity designed to receive center post 1210. Center post 1210 may extend completely through outer layer cylinder layer 1230 as pictured or may instead just come flush to the base of device 1200. The tapered shape of center post 1210 provides for a means of seating the implant while also providing a method for transferring mechanical stimulus to all sections of the subchondral bone region. When downward force 1250 is applied to device 1200 outer cylinder layer 1230 is experiences outward force 1240 thus providing improved seating of device 1200 into a cored bone void. Thus forces applied to cartilage layer 1220 pass into center post 1210 and are transferred to the tissue void.

Figure 13:
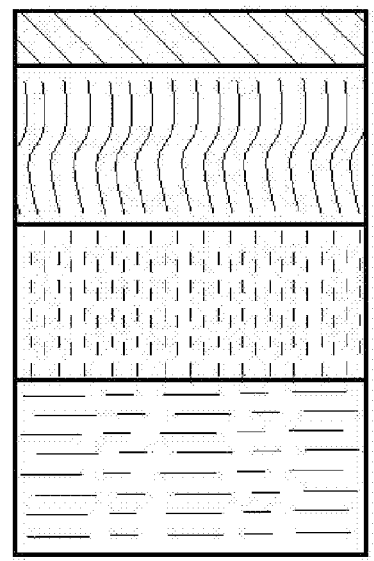
FIG. 13 is a depiction of a multi-layered cylinder comprising various material thicknesses and densities, where the layers can serve to transmit forces or loads through the device to underlying tissue below.

FIG. 13 is composed of a multi-layered cylinder containing various material thicknesses and densities. The layers can be constructed to act to transfer the pressure between the top surface of the device and the bottom surface. The composition of these various layers can also be utilized to create hydraulic swelling to thereby create the spring-like effect previously described.

Figure 14A:
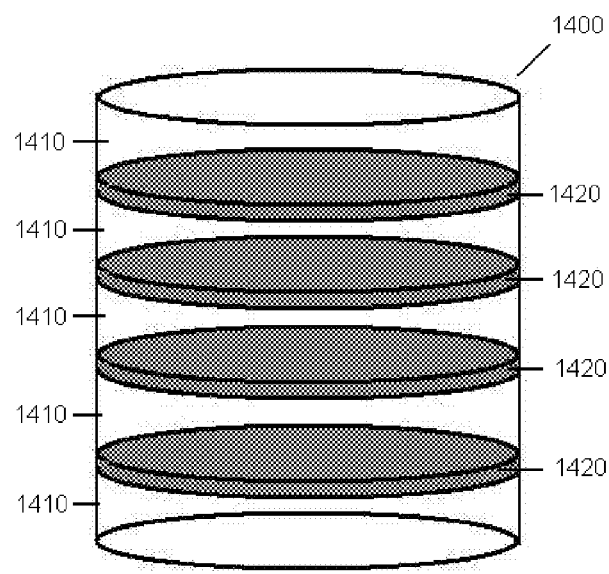
FIGS. 14a and b are depictions of a multi-layered cylinder material having swellable properties upon hydration, and capable of transmitting forces hydraulically through the device to the underlying tissue below.
Figure 14B:
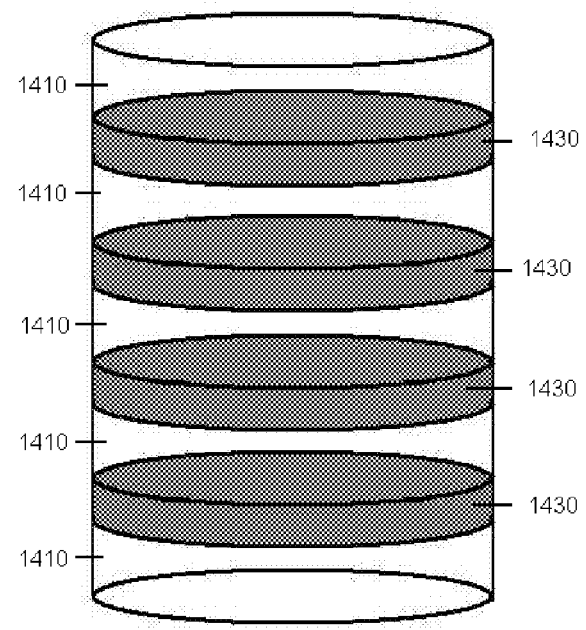

FIG. 14a shows a simplified example of a bone region multi-layered cylinder 1400. To simplify understanding, the cartilage layer is not pictured. Swellable layers 1420 separate rigid porous layers 1410. More or less layers are also contemplated. Upon implantation or exposure to liquid, swellable layers 1420 imbibe fluid and become an uncompressible, flexible hydrogel as depicted in FIG. 14b where rigid porous layers 1410 are now separated by swollen layers 1430. Referring to FIG. 14b, a force applied to the cartilage layer (not shown) is transferred as a pressure wave through the device so long as rigid porous layers 1410 do not exceed 4 mm in thickness and have an average porosity greater than 50 microns and are rigid enough to avoid collapse of their porosity thus not dissipating the pressure wave prior to it reaching the bottom layer and finally being conducted into the underlying bone. Optionally one or more holes, 2 millimeters in diameter or greater can exist in layers 1410 allowing pillars of hydrogel to connect swollen layers 1430. It may be I that newly forming bone needs a stable substratum to attach to so that bone forming cells can lay down extracellular matrix. Bone forming cells known as osteoblasts are approximately 50 microns in diameter and should establish themselves in newly forming islands of bone approximately 1 mm in diameter, thus the minimum thickness of porous layer 1410 is 1 millimeter. The thickness of swollen layer 1430 has no maximum, but should be at a minimum of 5 microns with a preferred thickness of 50 microns to trap a sufficient amount of fluid and thus function as an incompressible hydrogel capable of transferring pressure waves.

In another embodiment (not shown) porous particles having a minimum approximate diameter of 1 millimeter can be surrounded by a swellable material wherein the swellable material maintains connectivity throughout the entire device. In this way, pressure waves and micro motion, necessary for establishing bone external to the device, can be conducted through the swellable material matrix while the porous particles provide a stable platform for attachment and proliferation of osteoblasts. As a non limiting example, porous particles composed of ceramic, polymer or composites of the two can be suspended within a hydrogel forming material such as collagen, hyaluronic acid, chitosan, alginate, keratin, or PEG. In addition to being a homogenous material, the hydrogel can be formed into a porous network presenting fluid swollen struts or partitions defining fluid containing pores.

The bone region of all the above devices can be designed so that they provide the required expansion and transfer of force as the materials degrade. This transfer of force can occur through the use of rigid polymeric or ceramic elements, incompressible hydrogels or combinations thereof. As more cells are stimulated to grow into the implanted matrix, newly formed tissue will help to continue the transfer of the mechanical stimulation.

The inclusion of groups and subgroups in the tables is exemplary and for convenience only. The grouping does not indicate a preferred use or limitation on use of any material therein. For example, in Table 1, the groupings are for reference only and not meant to be limiting in any way. Additionally, the tables are not exhaustive, as many other drugs and drug groups are contemplated for use in the current embodiments. There are naturally occurring and synthesized forms of many therapies, both existing and under development, and the table is meant to include both forms.

Numerous other embodiments and modifications will be apparent to those skilled in the art and it will be appreciated that the above description of a preferred embodiment is illustrative only. It is not intended to limit the scope of the embodiments contained herein, which are defined by the following claims. Without further elaboration the foregoing will so fully illustrate our invention that others may, by applying current or future knowledge, adopt the same for use under various conditions of service.

TABLE 1

Examples of Biologically Active Agents

Adenovirus with or without genetic material
    Angiogenic agents
        Angiotensin Converting Enzyme Inhibitors (ACE inhibitors)

TABLE 1-continued

Examples of Biologically Active Agents

Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antimicrobial
Antioxidants
Anti-platelet agents
    Forskolin
Anti-proliferation agents
Anti-rejection agents
    Rapamycin
Anti-restenosis agents
Antisense
Anti-thrombogenic agents
    Argatroban
    Hirudin
    GP IIb/IIIa inhibitors
Anti-virus drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
    Adipose cells
    Bone marrow cells
    Blood cells
    Endothelial Cells
    Epithelial cells
    Skeletal muscle cells
    Smooth muscle cells
    Stem Cells
    Umbilical cord cells
    Fat cells
    Bone cells
    Mesenchymal stem cells
    Progenitor cells
    Cartilage cells
Cellular Material
    Bone marrow
    Cells with altered receptors or binding sites
    Fibroblasts
    Genetically altered cells
    Glycoproteins
    Growth factors
    Lipids
    Liposomes
    Macrophages
    Reticulocytes
    Vesicles
Chemotherapeutic agents (e.g. Ceramide, Taxol, Cisplatin)
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Acidic fibroblast growth factor (aFGF)
    Autologous Growth Factors
    Basic fibroblast growth factor (bFGF)
    Bone morphogenic proteins (BMPs)
    Bovine Derived Growth Factors
    Cartilage Derived Growth Factors (CDF)
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived endothelial cell growth factor (PD-ECGF)
    Platelet Derived Growth Factor (PDGF)
    Recombinant NGF (rhNGF)
    Recombinant Growth Factors
    Tissue Derived Cytokines
    Tissue necrosis factor (TNF)
    Transforming growth factors alpha (TGF-alpha)
    Transforming growth factors beta (TGF-beta)
    Tumor necrosis factor alpha (TNF-.alpha.)
    Vascular Endothelial Growth Factor (VEGF)
    Vascular permeability factor (UPF)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interlukin-8 (IL-8)
Interlukins
Lipid lowering agents
Lipo-proteins
Liposomes
Lipids
Low-molecular weight heparin
Lymphocites
Lysine
MAC-1
Morphogens
Nitric oxide (NO)
Nucleotides
n-methylpyrrolidinone (NMP)
Dimethyl Sulfoxide (DMSO)
Peptides
Phosphorylcholine
Phospholipids
Polypeptides
PR39
Proteins
Prostaglandins
Proteoglycans
    Perlecan

TABLE 1-continued

Examples of Biologically Active Agents

Radioactive materials
    Iodine - 125
    Iodine - 131
    Iridium - 192
    Palladium 103
Radio-pharmaceuticals
Secondary Messengers
    Ceramide
Somatomedins
Statins
Steroids
Sulfonyl
Thrombin
Thrombin inhibitor
Thrombolytics
Ticlid
Tyrosine kinase Inhibitors
    ST638
    AG-17
Vasodilator
    Histamine
    Forskolin
    Nitroglycerin
Vitamins
    E
    C
Yeast

TABLE 2

Examples of Materials and Additives

Aliphatic polyesters
Cellulose
Bioglass
Chitin
Collagen
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
Organic Solvents
PHBA/γ-hydroxyvalerate copolymers (PHBA/HVA)
PLA/polyethylene oxide copolymers
PLA-polyethylene oxide (PELA)
Poly (amino acids)
Poly (trimethylene carbonates)
Polyhydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)

TABLE 2-continued

Examples of Materials and Additives

Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers
Alginate
Calcium
Calcium Phosphate
Calcium Sulfate
Ceramics
Chitosan
Cyanoacrylate
Collagen
Dacron
Demineralized bone
Elastin
Keratin
Plasticizers
Fibrin
Gelatin
Glass
Gold
Glycosaminoglycans
Hyaluronic acid
Hydrogels
Hydroxyapatite
Hydroxyethyl methacrylate
Hyaluronic Acid
Liposomes
Lipids
Nitinol
Nanoparticles
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium
Silica
Clay
Metals
Silver
Aluminum Oxides
Ceramics
Polymers
Metal Oxides
Alkyl methlacrylates
Hydrophilic polymer
Integrins
Paralyne
Polyacrylamide
Polyanhydrides
Polyethylene acetate
Polyethylene glycol
Polyethylene oxide TABLE 2-continued Examples of Materials and Additives Polyurethane
Polyvinyl alcohol
Polyvinyl pyrrolidone
Silanes
Silicone

What is claimed is:

1. A device for repair or replacement of tissue deficiencies in a living being, comprising at least two juxtaposed materials that form a malleable matrix capable of transmitting forces in the form of a vortex ring, with a first material of said at least two juxtaposed materials presenting itself as a hydrogel capable of receiving and accumulating desirable factors or molecules from surrounding fluid when exposed to dynamic loading, said hydrogel encapsulating a second material of said at least two juxtaposed materials, the second material being in the form of a three-dimensional network of fibers, wherein the fibers making up the network of fibers are interwoven or knitted, thereby forming connecting nodes or knots, and the distance between connecting nodes or knots is not less than 2 millimeters and not more than 1.5 times a diameter of said device, wherein said device is formed as a plug having a circular cross-section and shaped to fill a void or defect created through a cartilage layer and into underlying bone, wherein the three-dimensional network of fibers are randomly located within said hydrogel, and further wherein said device is at least partially resorbable by the living being.

2. The device of claim 1 wherein the matrix is porous.

3. The device of claim 1 wherein the matrix is configured to become malleable upon hydration.

4. The device of claim 1 wherein the matrix is configured to return to its original shape after deformation.

5. The device of claim 1 wherein the fiber material is suspended within the hydrogel material.

6. The device of claim 1 wherein the matrix also contains an additive in the form of a particulate or biologically active agent.

7. The device of claim 1 wherein the juxtaposed materials are selected from the groups consisting of ceramics, natural polymers, synthetic polymer and combinations thereof.

8. The device of claim 1 wherein the matrix is attached to a porous rigid base.

9. The device of claim 1 wherein the matrix is attached a rigid base material selected from the groups consisting of metals, polymers, ceramics or combinations thereof.

10. The device of claim 1, wherein the second material comprises collagen.

11. A device for repair or replacement of tissue deficiencies, comprising at least two juxtaposed materials that form a malleable matrix capable of transmitting forces in the form of a gyre, wherein a first material of said at least two juxtaposed materials is a collagen hydrogel, said collagen hydrogel encapsulating a second material of said at least two juxtaposed materials, the second material being in the form of a three-dimensional network of collagen fibers, wherein the fibers making up the network of collagen fibers are interwoven or knitted, thereby forming connecting nodes or knots, and the distance between connecting nodes or knots is not less than 2 millimeters and not greater than 1.5 times a diameter of said device, wherein said device is formed as a plug having a circular cross-section and shaped to fill a void or defect created through a cartilage layer and into underlying bone, wherein the three-dimensional network of collagen fibers are randomly located within said collagen hydrogel.

12. The device of claim 11, wherein the matrix is porous.

13. A device for repair or replacement of tissue deficiencies, comprising at least two juxtaposed materials that form a malleable matrix, said juxtaposed materials comprising a hyaluronic acid hydrogel encapsulating a three-dimensional network of chitosan fibers, wherein the fibers making up the network of chitosan fibers are interwoven or knitted, thereby forming connecting nodes or knots, and the distance between connecting nodes or knots is not less than 2 millimeters and not greater than 1.5 times a diameter of said device, wherein said device is formed as a plug having a circular cross-section and shaped to fill a void or defect created through a cartilage layer and into underlying bone, wherein the three-dimensional network of chitosan fibers are randomly located within the hyaluronic acid hydrogel.

14. The device of claim 13, wherein the matrix is porous.

* * * * *